(12) United States Patent
Afeyan et al.

(10) Patent No.: US 6,344,172 B1
(45) Date of Patent: Feb. 5, 2002

(54) PROTEIN CHROMATOGRAPHY SYSTEM

(75) Inventors: Noubar Afeyan; Neal F. Gordon, both of Brookline, MA (US)

(73) Assignee: PerSeptive Biosystems, Inc., Framingham, MA (US)

( * ) Notice: Subject to any disclaimer, the term of this patent is extended or adjusted under 35 U.S.C. 154(b) by 0 days.

(21) Appl. No.: 08/333,880

(22) Filed: Nov. 3, 1994

Related U.S. Application Data

(63) Continuation of application No. 08/032,732, filed on Mar. 15, 1993, now abandoned, which is a continuation of application No. 07/805,066, filed on Dec. 11, 1991, now abandoned, which is a continuation-in-part of application No. 07/769,118, filed on Sep. 30, 1991, now abandoned.

(51) Int. Cl.[7] ............................................. G01N 30/02
(52) U.S. Cl. ........................... 422/70; 422/81; 422/103; 210/656; 210/198.2
(58) Field of Search .................. 422/70, 81, 103; 210/656, 198.2, 96.1

(56) References Cited

U.S. PATENT DOCUMENTS

| | | | | |
|---|---|---|---|---|
| 4,271,697 A | * | 6/1981 | Mowery, Jr. ................. | 422/70 |
| 4,724,081 A | * | 2/1988 | Kawahara et al. ........ | 210/198.2 |
| 4,840,730 A | * | 6/1989 | Saxena et al. ........... | 210/198.2 |
| 4,859,342 A | | 8/1989 | Shirasawa et al. | |
| 4,981,804 A | * | 1/1991 | Hanaoka et al. .............. | 422/70 |
| 5,019,270 A | | 5/1991 | Afeyan et al. ............... | 210/656 |
| 5,030,352 A | | 7/1991 | Varady et al. ............ | 210/502.1 |
| 5,071,547 A | * | 12/1991 | Cazer et al. .............. | 210/198.2 |
| 5,104,622 A | * | 4/1992 | Binder ........................ | 422/70 |
| 5,117,109 A | * | 5/1992 | Asakawa et al. ......... | 210/198.2 |
| 5,135,718 A | * | 8/1992 | Kawaguchi et al. ........... | 422/70 |

FOREIGN PATENT DOCUMENTS

| | | |
|---|---|---|
| DE | 3002996 | 7/1981 |
| EP | 0103082 | 3/1984 |

OTHER PUBLICATIONS

Afeyan et al., *BiooTechnology*, 8:203–206 (1990).
Hearn, *J. Chromatography*, 418:3–26 (1987).
Regnier, *J. Chromatography*, 418:115–143 (1987).
Little, "Column Switching Techniques In Modern HPLC", *International Laboratory*, 14:26–34, (1984).
Schaefer, "An HPLC System With Next Generation Diode Array Technology", *International Laboratory*, 20:6,8–12, 14–15 (1990).
Sutfeld *J. Chromatography*, 464:103–115 (1989).

* cited by examiner

*Primary Examiner*—Long V. Le
*Assistant Examiner*—Gary W. Counts
(74) *Attorney, Agent, or Firm*—Testa, Hurwitz & Thibeault, LLP

(57) ABSTRACT

The invention features an apparatus for the separation and analysis of proteins, which includes a sample input, a first liquid chromatography column, a multiport injection valve connecting the sample input to the column, a pump for providing variable pressure delivery of a solution to the column via the multiport valve, and a program for specifying a sequence of system control programs.

17 Claims, 23 Drawing Sheets

Regenerate reverse phase column 131
by cleaning and washing;

Load sample on reverse phase column 131:

set valve 116 to sample port
　　and pull sample into loop 152
　　using pump 119;
switch valve 151 to state 2;

Elute sample on reverse phase column 131
and apply to antibody column 132:

switch valve 133 to state 1
　　to put column 132 on-line;
set valve 112;
operate pump 113;

store data;

Regenerate both columns elute and wash by placing
　　valve 151 in state 2,
　　valve 134 in state 1, and
　　valve 133 in state 1.

FIG. 13B

Pre-equilibrate column 131:

> set valve 151 to state 1,
> valve 134 to state 2, and
> valve 133 to state 2;
> set valve 112 to draw and
>   mix selected buffers;
> operate pump 113 to draw
>   buffer mix through valves
>   151 and 134
>   and columns 131;

Load sample on solute-binding column 131:

> set valve 116 to sample port
>   and pull sample into loop 152
>   using pump 119;
> switch valve 151 to state 1
>   to deliver sample to column 131;
> pass effluent directly to detector 136;

> store data;

> continue passing new sample over
>   column 131 and measuring
>   concentration of effluent
>   from column 131 in detector 136
>   until column 131 effluent
>   concentration rises and plateaus;

> store data and calculate concentrations;

FIG. 14A

Check data by eluting solute from column 131:

> Pass elution buffer through
>     column 131 via valves 151
>     (state 2), 134 (state 2);
>     and 133 (state 2);
> detect, store and calculate concentration;

Regenerate column

> Clean and wash by placing
>     valve 151 in state 2;
>     valve 134 in state 2; and
>     valve 133 in state 2.

FIG. 14B

Pre-equilibrate columns 131 and 132:

> set valve 151 to state 1,
>   valve 134 to state 2, and
>   valve 133 to state 1;
> set valve 112 to draw and
>   mix selected buffers;
> operate pump 113 to draw
>   buffer mix through valves
>   151, 134, 133,
>   and columns 131 and 132;

Load sample on solute-binding column 131:

> switch valve 151 to state 2
>   to deliver sample to column 131;
> switch valve 133 to state 2
>   to bypass column 132 and
> pass effluent directly to detector 136;

> store data;

> continue passing new sample over
>   column 131 and measuring
>   concentration of effluent
>   from column 131 in detector 136
>   until column 131 effluent
>   concentration rises
>   (i.e., breaks through) and plateaus;

> store data and calculate concentrations;

FIG. 15A

Pass breakthrough over column 132:

> when column 131 breakthrough
>    is detected, put column 132
>    on-line by switching
>    valve 133 to state 1;
>
> pass 131 effluent over column 132
>    and to detector 136;
>
> store and calculate concentration;

Regenerate both columns

> Elute and wash by placing
>    valve 151 in state 2,
>    valve 134 in state 1, and
>    valve 133 in state 1.

FIG. 15B

Equilibrate columns 131 and 132:

> set valve 151 to state 1,
> valve 134 to state 2, and
> valve 133 to state 1;
> set valve 112 to draw and
> mix selected buffers;
> operate pump 113 to draw
> buffer mix through valves
> 151, 134, 133,
> and columns 131 and 132;

Load sample on ion exchange column 131:

> switch column 132 off-line by
> switching port 133 to state 2;
> set valve 116 to sample port and
> pull sample into loop 152
> using pump 119;
> switch valve 151 to state 2 to
> deliver sample to column 131;

FIG. 16A

PROTEIN CHROMATOGRAPHY SYSTEM

This is a continuation of Ser. No. 08/032,732 filed on Mar. 15, 1993, now abandoned, which is a continuation of copending application(s) Ser. No. 07/805,066 filed on Dec. 11, 1991, which is a CIP of Ser. No. 07/769,118 filed Sep. 30, 1991 now abandoned.

This invention related to a system useful in chromatography procedures.

BACKGROUND OF THE INVENTION

Chromatographic techniques are well known in the art as means for separating components (solutes) present in a mixture. These techniques are particularly useful in the chemical and biotechnological arts. True chromatography describes the separation of solutes according to their different partitioning between two (or three) phases. The phases generally are solid and liquid, and solute partitioning results in their differing mobilities through a layer of solid, typically particulate, matrix in the presence of a flowing phase. Solute transfer through the layer may be along a pressure gradient, generally referred to as "liquid chromatography". Typically, the sample to be separated is applied to a column filled with pellets or grains of a chromatography separation medium, and a solvent flow is maintained through the column at a steady rate. Components of the mixture are carried along by the solvent flow until each substance exits the column as a "peak" in the output, different peaks being more or less broad and overlapping.

Chromatographic matrices can separate components by any of a number of criteria, including size, electrical charge, hydrophobic interaction, and/or specific affinity for the matrix or binding sites thereon. Because the components in the mixture will vary in their affinity for the matrix, their partitioning as they pass through the matrix separates the components so that they exit the matrix sequentially, separated temporally and spatially. Determination of the location of the various separated components, or of a given component of interest within the sequence, generally is achieved by collecting the fluid phase exiting the matrix (i.e., the effluent stream) as a series of fractions and sampling these fractions to identify their contents by any of a number of means known in the art.

Resolution of the various components in the mixture depends on several considerations, chief among them being the partitioning ability of the matrix and the system's theoretical plate height and plate number (see infra). In general, a large surface area-to-volume ratio is desired. Matrices for liquid chromatography systems typically are housed in cylindrical chromatography systems known as columns. In electrophoresis systems, high resolution also demands efficient removal of the heat generated by the applied electric field. Capillary electrophoresis, or other electrophoretic modules which provide a large surface area-to-volume ratio dissipate Joule heat well, allowing rapid analysis without significant loss of resolution.

Techniques are known for treating the chromatography medium to enhance the affinity of the column generally for cationic or anionic substances, or to cause a reversible bonding to particular chemical groups or biologically active materials, so that samples containing these groups or materials may be releasably bound to the column and subsequently eluted.

To achieve a particular separation, the general practice of chromatographic separation involves identifying or selecting a particular medium or coated medium, and an optimum solvent, solvent flow rate, pH, ionic concentrations and other environmental conditions, such that the starting mixture will separate into a number of relatively narrow bands and such that at least the substance of interest passes, or may be made to pass, as a distinct output.

The determination of an appropriate set of separation conditions for a particular substance, which may have an as yet undetermined chemical structure and conformation and unknown chromatographic affinities, is a task that involves experience, experimentation, intuition and luck. Because of the complex dependence of the transport and adsorption mechanisms of biomolecules on multiple different conditions, further experimentation is usually necessary even when it is desired only to scale up a known process to operate at greater speed or to utilize a larger column. In order to meet the separation objectives of high purity, high speed and/or high volume separation, a very large number of separation conditions must be experimentally analyzed to determine one suitable set of operating conditions.

In general, the transport of material in a separation column proceeds on a macroscopic level by flow past and between the grains or pellets of the chromatography medium, while the degree of separation and column capacity are governed more by the rates at which the particular components diffuse along branching paths into and out of pores in the medium, and are repeatedly adsorbed and released along the diffusion path. By increasing the flow rate to increase process output, one generally broadens the eluted peak width of each component, thus sacrificing the resolution and hence the purity of the separated components; above a certain flow rate threshold, premature solute breakthrough may occur.

The need to monitor a product's status during its synthesis or purification is well known in the art. Status monitoring is particularly important in multistep preparation protocols. Frequently, the identity and, often, the quality of a product in a mixture must be determined at each step. Product monitoring also may be used as part of a feedback system to adjust process parameters. Generally, identification is determined using a previously established criterion for identification, for example, a characteristic absorbance measured at a given wavelength. If the product of interest is a protein, identification also may be by molecular weight, activity, and/or immunoaffinity.

It is an object of the invention to provide a rapid, adaptable, and repeatable system and apparatus for identifying the presence and/or location of a molecule of interest during any preparative or analytic protocol. The ultimate goal is to separate one or more components of a protein mixture by exploiting the benefits of high speed chromatographic techniques. Objects of the invention include two dimensional analysis to enhance resolving power of a chromatographic system, real time monitoring of solute concentration in a process mixture, detection of trace solute contaminants in a solution that contains a major amount of a dissolved product, rapid determination of the presence and location of a solute in a chromatography effluent during, e.g., any step of a preparative procedure, production of a profile of a mixture representative of the nature and relative concentration of structured variants of a given solute, and the rapid assessment of the success of a purification or separation protocol.

SUMMARY OF THE INVENTION

The invention features an apparatus and methods for the rapid and efficient separation of proteins and other biological macromolecules. The apparatus includes sample input means, a first liquid chromatography column, a multiport injection valve connecting the sample input means to the column, a second chromatography column in communication with the multiport injection valve, the second column being operative successively with or alternatively to the first column, pump means for providing variable pressure delivery of a solution to the column via the multiport valve, and program means for specifying a sequence of system control programs.

In preferred embodiments, the apparatus further includes control means in communication with the pump means for controlling the pressure of delivery of the solution; and solution input means including plural solution reservoirs, and a mixing valve, connecting the solution input means to the sample input means, operative to mix solution from the reservoir, wherein the program means specifies the mixing of solution by the mixing valve, and the delivery of the mixed solution to the column via the multiport injection valve; and detector means for detecting and recording column output; and matching means for identifying a pattern of detected output data, the template matching means being operatively keyed to means for developing a control program for liquid chromatography separation.

In another embodiment, the invention features an apparatus for the separation of proteins, which includes first and second liquid chromatography columns, means for introducing a solution into a first said column, multiple multi-port valves in communication with the first and second columns through which solution is transported, and output means comprising a detector and data collector.

Preferably, this embodiment includes pump means for introducing solution into the first column; control means in communication with the pump means for controlling the pressure of delivery of the solvent. Preferably, the multiple valves include first, second, and third valves, and the solution is introduced through the first and second valves into the first column, through the second and third valves into the second column, and through the third valve into the output means. The first valve also includes multiple ports which communicate with each other in an adjacent clockwise or counterclockwise direction, and a loop connecting two non-adjacent ports. The solution introducing means comprises sample input means which includes a sample reservoir. The sample input means may further include a sample pump, and the solution introducing means may include plural solution reservoirs, a valve for selection and mixing solutions, and a pump for delivering solution to the first column. The output means may further include a fourth multi-port valve connecting the detector to the data collector. The detector may be a UV detector. The output means may further include a pH/conductivity detector in communication with the UV detector and the data collector through the fourth multi-port valve.

Preferably, the column has a first and a second end and at least one of the first or second columns is packed with a chromatography matrix which confers on the packed column a transit time from the first to the second end of less than five minutes. The chromatography matrix itself may be perfusive.

In another embodiment of the invention, the apparatus includes a multiport mixing valve for mixing sample with one or more buffers to produce a sample mix, plural liquid chromatography columns, each column includes a first and a second end, a multiport injection valve in communication with the sample mixing valve and the first end of each of the chromatography columns, an output system including at least one of an output signal recording system and an output sample collection system, wherein the output system is in communication with the second end of each of the columns, and controls means for operating the multiport injection valve to successively and alternately apply the mixed solution from the mixing valve to the first and to the second column in coordination with operation of the output system to run a sequence of separations for the preparation or analysis of a protein.

Preferably, the apparatus further includes a sample input system comprising plural solution reservoirs and a sample reservoir.

In another embodiment, the apparatus further includes plural chromatography columns, each column packed with a particulate matrix separation medium and having a characteristic transit time for proteins of under five minutes between a column input and a column output ends, sample input means including an input valve for delivery of solutions to one column at the column input end and a multiport valve for mixing solutions provided to the input valve, column output means for detecting column output including means for detection and providing a signal indicative thereof, and control means for operating the sample input means to perform a sequence of successive separations in one column by providing in successive separation cycles different mixes of fluids to the input valve. The control means may further include switching means for alternatively utilizing one of the chromatography columns while cleanng another, thus providing a substantially continuous operating sequence of outputs from successively utilized columns. The apparatus may further include program means for specifying a sequence of separation process control programs to be successively run during operation. The program means may specify a separation program in which first and second columns are utilized successively for separating proteins in the sample.

Preferably, one column of the apparatus includes an ion exchange chromatography matrix. Alternatively or additionally, one column may include a reverse phase chromatography matrix. The apparatus is preferably used for preparation and analysis of a sample, where the first column specifies a preparative parameter and the second column specifies an analytical parameter. The program may thus specify a substantially continuous preparation of a separated sample in the first column and intermittent analysis of the first column output via the second column. Each of the first and second columns, individually, may be removable and replaceable by third and fourth columns, respectively.

In another embodiment, the apparatus includes first and second multiport valves, each valve including a sample loop, for holding a defined sample volume, connecting two ports of each valve, a liquid chromatography column in communication with each valve, a sample feed line in communication with each valve, detector means in communication with the second valve for detecting output, and control means for operating the multiport valves to switch between a collection line comprising the sample feed line wherein plural sample volumes are introduced and a detection line including the chromatography column, wherein one sample volume is passed through the detector means and another is passed through the column and detector means.

In preferred embodiments, the collecting line further includes in successive order (a) the first sample loop connecting within the first valve a first port to a second port, (b) the sample feed line connecting the first valve second port with the second valve first port, and (c) the second sample loop connecting within the second valve the first port to the second port. The detection line may further include in successive order (a) the first sample loop connecting within the first valve a first port to a third port, (b) the chromatography column connecting the first valve third port with the second valve third port, (c) the second sample loop connecting within the second valve the third port to the second port, and (d) a shunt connecting the second valve second port with the detector. In other preferred embodiments, additional multiport valves may be present; for example, a third multiport valve positioned in order between the first and the second valves, and connecting the chromatography column to these valves.

In this embodiment of the invention, the apparatus is capable of holding two defined volumes of sample, a non-adsorbed sample which has bypassed the column and an adsorbed sample which has passed through the matrix and thus lacks most of the target solute. The adsorbed sample solution will exit the matrix in-line with the sample solution that bypassed the matrix and that is contained within the second sample loop. The two sample solutions will then flow through a detector and result in a graph with two well-defined peak That is, when the feed solution that bypassed the matrix reaches, the detector, a peak representative of the concentration of all solutes in the effluent, i.e., the target and nontarget solutes together, will result. This will be followed by a second peak representative of the concentration of non-target solutes only. The difference in peak areas divided by the area of the peaks representing total solutes in the sample is a measure of the purity of the sample.

Thus, all information necessary to calculate the target solute and/or impurities concentrations is available in a defined sample volume as soon as the sample has been passed through the column matrix. If desired, the target solute can be eluted from the matrix and its concentration can be determined independently of the concentrations of feed solution containing all solutes and the adsorbed solution containing only nontarget solutes.

Advantages of this embodiment of the invention include rapid monitoring of the presence, quantity, and/or purity of a target solute in a product sample, during a preparative procedure. The rapidity of the analysis, e.g., it can be performed in as little as 10 seconds, reduces the analytical burden of monitoring a preparative procedure and the downtime necessary to determine a subsequent preparative step. Impurities that are monitored in the rapid monitoring system include proteins, nucleic acids, endotoxins, or any biological molecule detectable in the sample.

In another aspect, the invention features methods of analyzing proteins of a sample. The methods include the following embodiments. One embodiment is a method of analysis of proteins of a sample which includes introducing a sample to a first column comprising an input and an output end, wherein the first column separates components of the sample and produces a first effluent stream of separated components, interrupting the first effluent stream at a predetermined position to collect a fraction of separated components, introducing the component portion to a second column, wherein the second column separates components of that fraction to produce a second effluent stream comprising separated components of the fraction, and detecting components of the second effluent stream.

Preferably, there is substantially continuous preparation of a separated sample in the first column and intermittent analysis of the first column output via the second column.

One column may include an ion exchange chromatography matrix; and/or one column may include a reverse phase chromatography matrix. The first column effluent may be diverted back to the first column input end via a multi-port valve, and this effluent may contain a substantially pure product. The second column may be designed to provide a pattern of output data determinative of the number of times the first effluent is diverted back to the first column input end. Preferably, a portion of the effluent stream may be directed to the second column by switching a multi-port valve.

In another embodiment, this aspect of the invention features a method of analysis of proteins of a sample, and includes introducing a sample to a first column comprising an input and an output end, wherein the first column separates components of the sample and produces a first effluent stream of separated components, diverting the first effluent stream to a second column comprising input and output ends that selectively removes a target component of the sample from the stream to produce a second effluent stream comprising substantially all components of the first effluent stream except the target component.

Preferably, the method further includes detecting the components of the first and second effluent streams.

In another embodiment, the invention features a method of analysis of proteins of a sample, which includes introducing a sample to a first column, wherein the first column, which includes input and output ends, selectively removes a target component from the sample to produce a first effluent stream comprising substantially all components of the sample except the target component, diverting the first effluent stream to a second column, comprising input and output ends, that separates components of the sample and produces a second effluent stream of separated components.

Preferably, this method includes detecting the output of the first and second effluent streams.

In another embodiment, the invention features a method of analysis of proteins of a sample which includes introducing a sample comprising a target protein and trace solutes to a first column, including input and output ends and a target-specific adsorbing means, wherein the first column selectively retains a target protein from the sample to produce a first effluent stream substantially lacking the target protein, diverting the first effluent stream to a second column, including input and output ends and a trace solute adsorbing means, that selectively adsorbs trace solutes from the stream to produce a second effluent stream, eluting the trace solutes from the second column, and detecting the eluted trace solutes.

Preferably, this method also includes a first column target adsorbing means which includes a target-specific affinity chromatography matrix, which may include be a target protein-specific immunoglobulin. Preferably, the trace solute adsorbing means comprises a means for nonspecifically binding proteins.

Preferably, in the embodiments of this aspect of the invention, the transit time between input of said sample into the input end of the first column and the output end of the second column is less than 10 minutes; most preferably, less than 7 minutes. The first effluent stream is directed to the second column by switching a multi-port valve. Each column may be packed with a particle matrix separation medium which confers on each column a characteristic transit time for proteins of under five minutes between each column input and column output ends. Preferably, the matrix is a perfusive chromatography matrix.

The methods and apparatus of the invention are rapid, reliable, and adaptable, and are particularly useful in the preparation of biological macromolecules, particularly in the separation and purification of proteins. The chromatography system described herein has advantages when used as a two column or one column system to separate components of a given sample; e.g., information from a first run may be used to calibrate a second run. The first and second columns may be readily regenerated with recycling solvents, allowing the systems to be used repeatedly throughout a given procedure. In addition, other advantages include automated preparation or analysis of a sample, e.g., a combined preparative/analytical procedure in which a first column is used to separate a component of a sample, and the second column is used to interrupt the purification procedure at any chosen time to assess the purity of the sample, thus providing a two-dimensional chromatographic analysis; analysis of the purity of a sample by removing the purified product in a first column, and concentrating and eluting contaminants in the second column; and analysis of both the concentration and purity of a product, and analysis of the product itself, i.e., structural variants which constitute the product peak or the proportion in the sample of pure product and impurities.

BRIEF DESCRIPTION OF THE DRAWINGS

These and other properties of the invention will be understood by those skilled in the art from the description herein, taken together with the drawings, wherein:

FIGS. 14(*a*) and (*b*) is a flow chart for operating the apparatus of the invention to perform breakthrough analysis of a sample;

FIGS. 15(*a*) and (*b*) is a flow chart for operating the apparatus of the invention to produce a structural profile of a breakthrough product.

DESCRIPTION OF PREFERRED EMBODIMENTS

Apparatus

Figure 1:
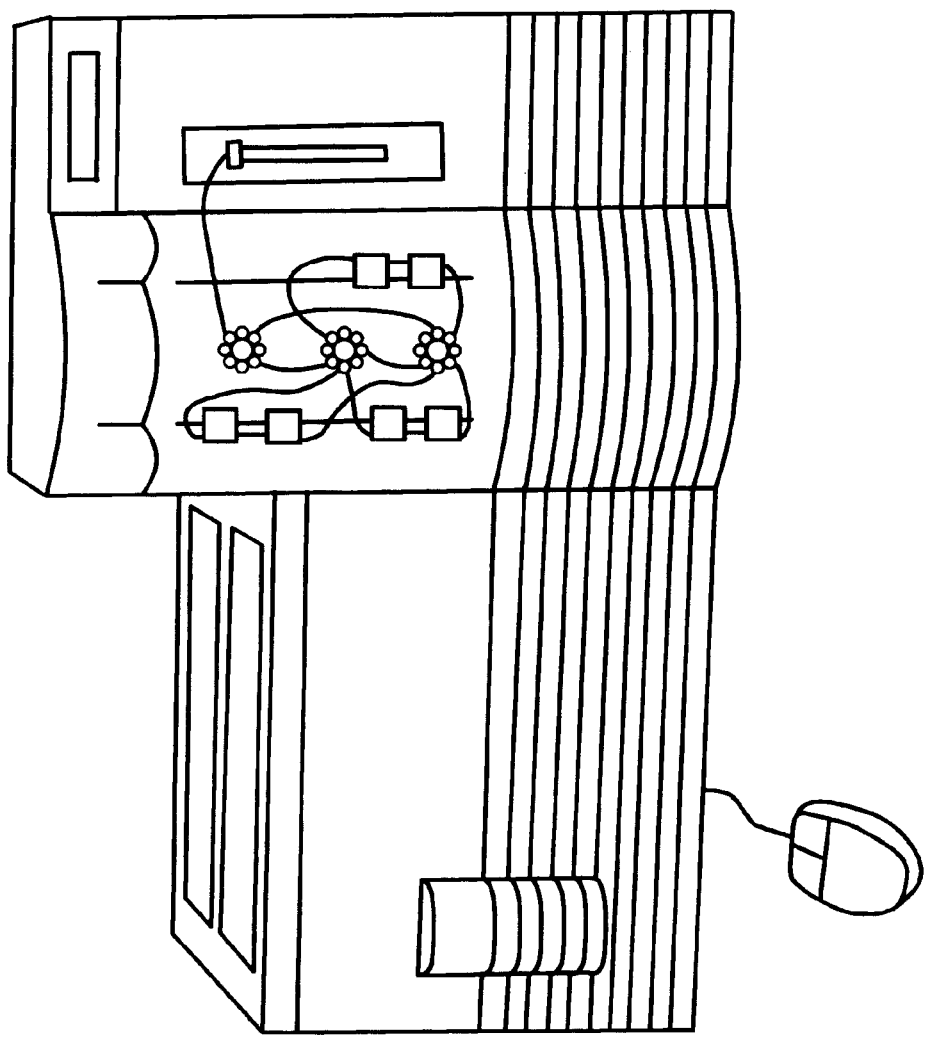
FIG. 1 is a drawing of a commercial embodiment of the invention.
Figure 1:
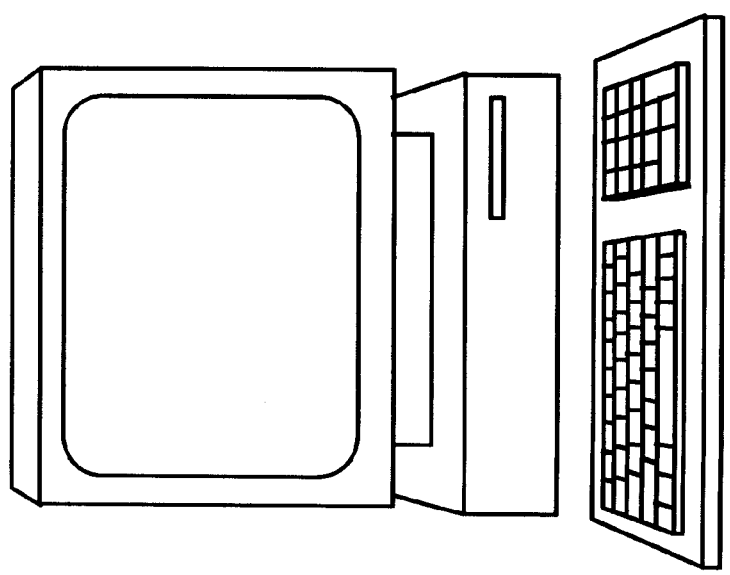

FIG. 1 is a drawing of a commercial embodiment of the invention, which shows the protein separation apparatus of the invention substantially enclosed in a housing, along with a computer keyboard, mouse, and terminal in which data is collected and stored, and in which program control sequences are stored and executed.

Figure 2:
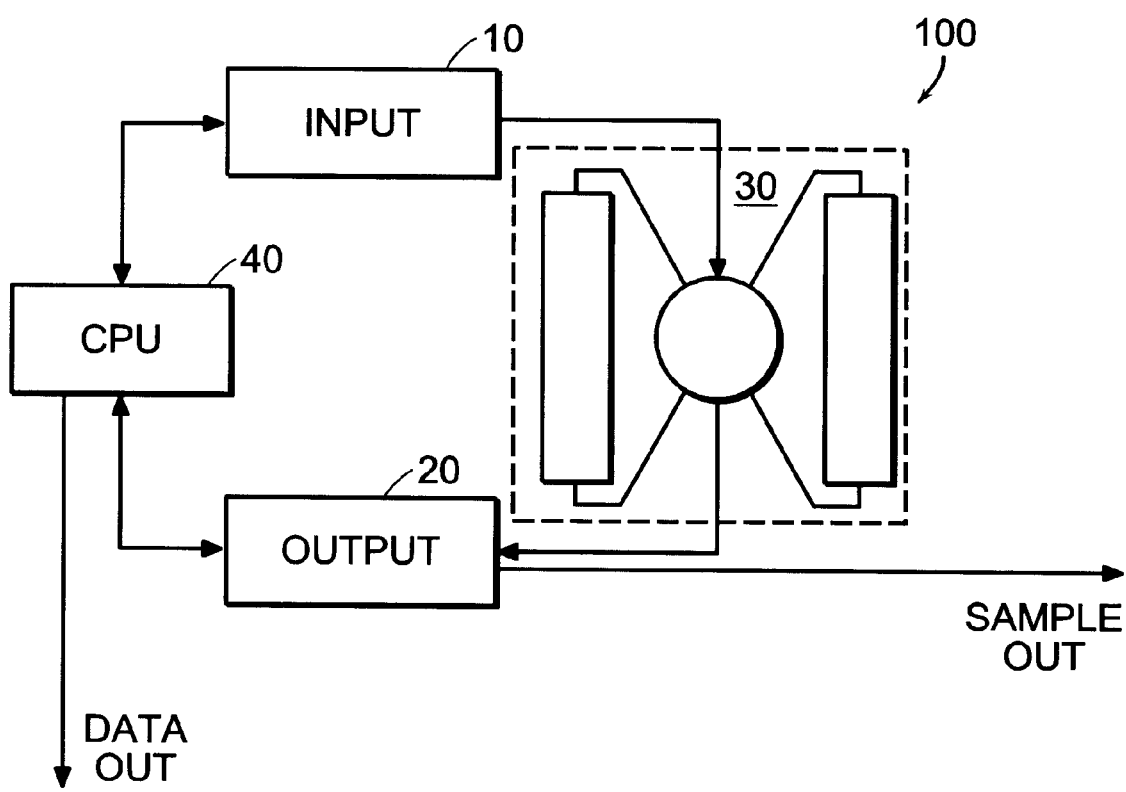
FIG. 2 is a schematic illustration of a system in accordance with the present invention.

Referring to FIG. 2, a general system 100 of components and control elements for the practice of the present invention is illustrated schematically, and includes an input section 10 which provides an input solution for a separation column, an output section 20 which develops output information signals from the column, a separation column section 30 which separates the samples received from the input section, and a processor 40 which receives information from the output section and controls operation of the input section and the separation column section to carry out a sequence of separations. In a degenerate operating mode, for use when an adequate set of separation conditions are known, the system may be operated to prepare useful amounts of a pure substance, by running repeated separations under identical operating conditions and passing the separated component from each run to a collection reservoir. In an analytical mode, samples are placed in an autosampler and run sequentially through the system, and data is collected. In both modes, the processor controls the input section to mix a predetermined carrier solution, and operates the sample delivery valves, column input valves and column output valves at appropriate times and in appropriate directions to perform the desired separation.

More generally, however, the device is operated to run a sequence of separations under different operating conditions, such that the output data constitute a matrix of separation results corresponding to different operating parameters. In this mode, the processor controls the input section to mix each of a series of different carrier solutions and to successively run a separation with each solution and tabulate the column results.

Figure 3:
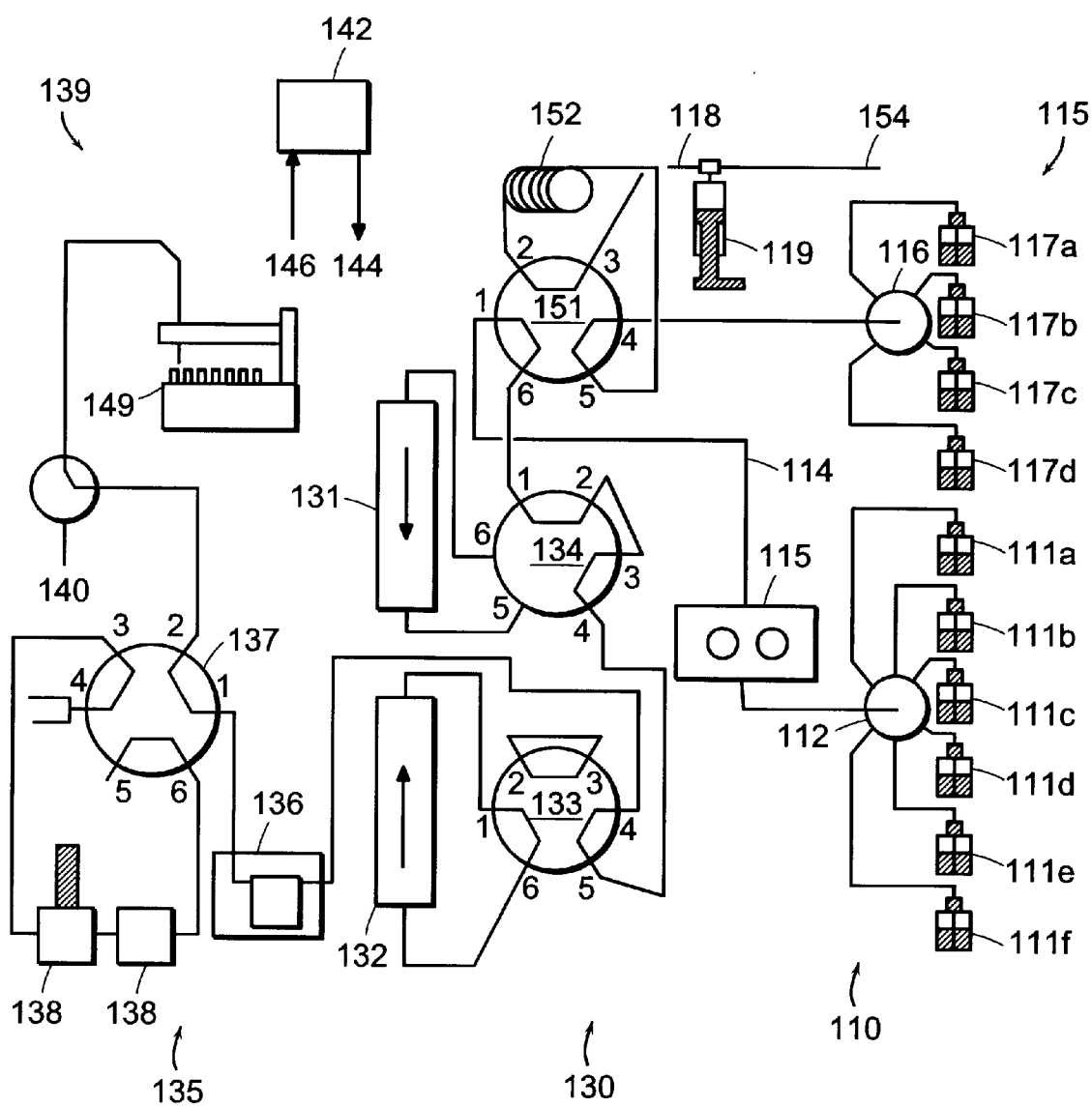
FIG. 3 is an illustration of an embodiment of the invention.

FIG. 3 illustrates in greater detail the hardware components of a presently preferred system 101 for the practice of the invention. A two column system of chromatography may be used according to the apparatus shown in FIG. 3; alternatively, other forms of the apparatus may be used, e.g., a one column system may be used by bypassing the second column, or a three column system may be used by attaching an additional column to the apparatus and bypassing one or two of the three columns. Referring to FIG. 3, a sample preparation section 115 and a solvent preparation section 110 each provide respective solutions to an input valve 151 connected to a separating column unit 130. An output section 135 receives the separation column output from unit 130 and develops electrical signals indicative of properties such as pH, conductivity and UV or other spectral absorbance or fluorescence. A processor section 142 receives and records the output information and controls the various other units to coordinate each separation run. Various peripheral devices allow display and manipulation of the output data or entry of control parameters.

In the sample input section 115, a four-way mixing valve 116 is connected to a plurality of reservoirs 117*a–d*, which may contain different samples or buffers; for example, bovine serum albumin (BSA), a cell culture aliquot, a base, or water. The output of mixing valve 116 is pumped along line 118 into a two-way six port valve 151, discussed further below, which also receives fluid from solvent input section 110. Sample pump 119, e.g., a syringe pump such as a stepper motor driven syringe pump, pulls sample through loop 152 from valve 116 and then discharges along line 118 to waste 154.

The solvent input or delivery system 110 includes a plurality of solvent reservoirs 111*a–f* connected to respective ports of a six port four-way mixing valve 112, the mixed output of which is fed to a high pressure pump 113 which in the prototype embodiments is a dual piston pump with a capacity of 60 ml/minute at 2000–3000 psi, the high pressure output being delivered along 114 to input valve 151 for supply to the separation columns. A suitable six port mixing valve can be obtained from BIOCHEM part no. 080T612 (Beantown, N.J.). Mixing of the sample with a solution or of different solvent solutions is accomplished by opening and closing the respective valves during the refill stroke of the pump. The solvents are then pulled into the pump and mixed within the pump as well as in a pulse damper at the pump outlet.

As briefly indicated above, operation of the mixing valve is controlled by a multichannel control system, the channels being denoted A, B, C, D, E, and F in a six channel embodiment, to provide a selected mixture of up to four different solvents from the reservoirs 111a–f, which may contain, for example, MES (2-[N-morpholino]ethane-sulfonic buffer, Tris-HCl and NaCl, water, and BSA, etc. One such mixing regimen will be described here, before continuing with a description of the separation and output portions of the apparatus.

In accordance with one preferred aspect of operation, the solvent reservoirs receive a set of different solvent mixtures, each containing two or three substances and useful over a wide pH range. For example two concentrated buffers (e.g., 100 mM) may be provided, each one adjusted to each extreme end of the desired pH range, e.g., one buffer adjusted to pH 6.0 and the other to pH 9.0, along with one concentrated eluent (e.g., 3.0 M NaCl) and water. The concentration of the target buffer is chosen (e.g., 20 mM), as is the pH and eluent concentration (e.g., 0.5 M NaCl). Either water or the salt solution may be used to dilute the buffers to the appropriate concentration. In operation, these mixing parameters may be exercised in a continuously-changing manner, to produce a gradient pH or ionic concentration variation during the course of one separation, or they may be held constant during each separation to effect a sequence of different experimental runs. As described further below, a variable, i.e., a gradient concentration, is preferably employed in certain elution steps.

Returning to FIG. 3, the mixed solvent from high pressure pump 113 and the sample from sample delivery section 115 are provided to ports (1) and (4), respectively, of the sample input valve 151. Valve 151 is a two-position three-channel valve, i.e., every other port is either placed in communication with the clockwise-adjacent port, or with the counter-clockwise adjacent port. Thus, in its first state, the sample at port (4) connects to port (5), is shunted through a fixed tube 152 to port (2) which connects to port (3) which in turn is connected to the sample pump and waste vessel 154, thereby filling the tube 152 with a sample from the input section 115. The remaining two ports (6) and (1) are connected so that the solvent provided by pump 113 to port (1) passes as an input from port (6) via ports (1) and (6) of valve 134 to the separation column section 130.

In the second state of valve 151, the solvent in high pressure line 114 is channeled from port (1) to port (2), pushing the previously-acquired sample in tube 152 to port (5) which connects to port (6), thus injecting the sample into the separation column section 130 and providing a continuing flow of solvent to effect the separation. The remaining port (4) connects to port (3) so that any flow from section 115 purges the sample line to a waste vessel, thereby setting up the line for a new sample of different pH, concentration, or the like.

Thus, valve 151 effectively receives sample in tube 152 and then provides a solvent flow to carry the sample through the separation column. As the separation proceeds, the mixing valve 112 may be operated to vary the solvent entering the system, to effect the different steps of washing, eluting, equilibrating and regenerating the columns for another run.

Figure 5:
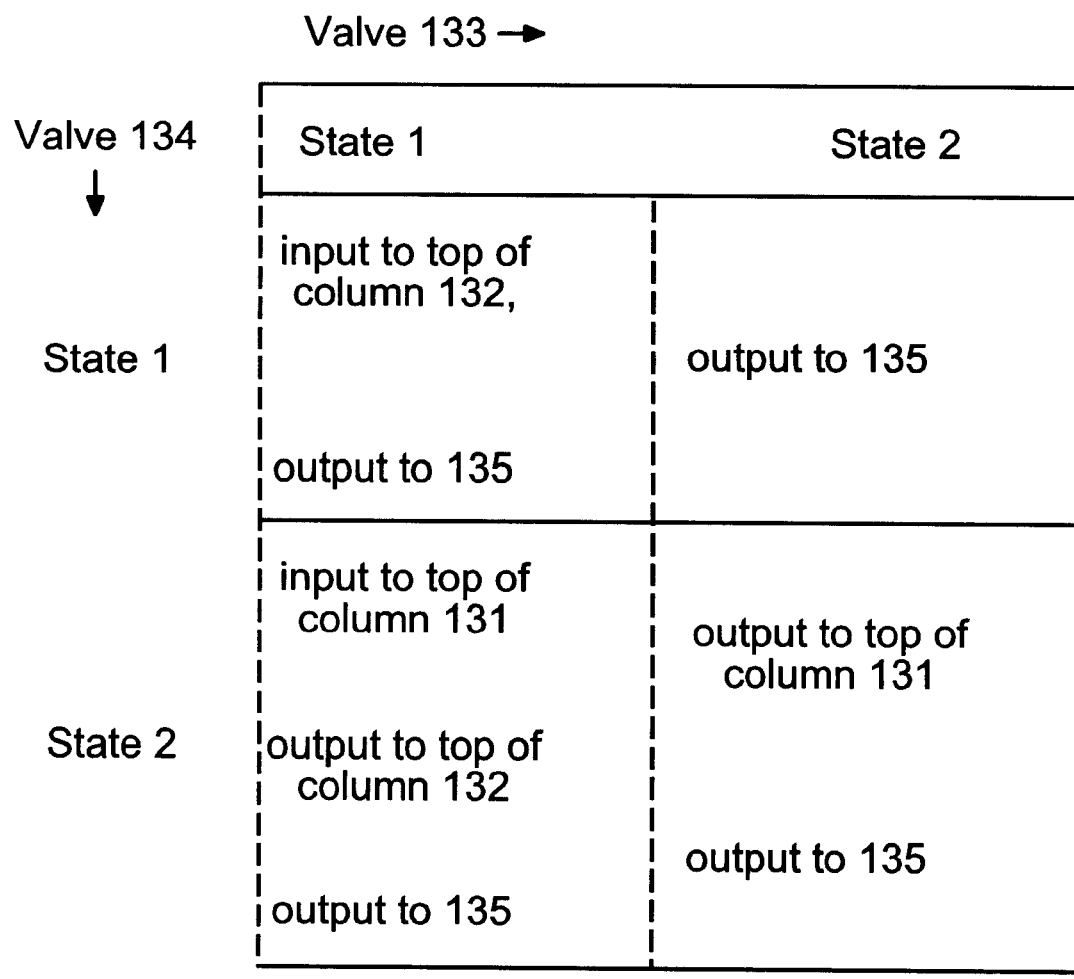
FIG. 5 is a state table for operation of multiple columns of the embodiment of FIGS. 4–6.

FIG. 3 shows a three valve, two column apparatus within the separation column section 130. A first column 131 and a second column 132 are connected as shown to another six port, two-position valve 133 which operates in conjunction with a similar valve 134 to direct the fluids received from valve 151 to one of the separation columns 131, 132 and to direct the output of the selected column to the output monitoring system State 1 is the valve state wherein ports 1 & 2, 3 & 4, and 5 & 6 are interconnected, while State 2 is the valve state wherein 6 & 1, 2 & 3, and 4 & 5 are interconnected, the four possible states of valves 133 and 134 operate to provide the input fluid to the top of either one, of the columns 131, 132 while passing the output to section 135, in accordance with FIG. 5. As shown in FIG. 5, if valve 133 is in state 1 and valve 134 is in state 1, only column 131 is on-line; if valve 133 is in state 2 and valve 134 is in state 1, both columns are off-line; if valve 133 is in state 1 and valve 134 is in state 2, both columns are on-line; and if valve 133 is in state 2 and valve 134 is in state 2, only column 131 is on-line.

In another embodiment of the invention, the columns may each be operated in a forward or backward direction, and may be backflushed, by a simple addition to the column valve system. A conventional constant flow pump, e.g., a peristaltic or piston pump, may be added to the system at port 4 of valve 134, to pump equilibration buffer through one column, e.g., column 132, while the other column, e.g., column 131, is being used for analysis or preparation of a product. Thus, sample can be introduced into column 131 as above, and eluant fed directly to the detector 136 while column 132 is being regenerated via buffer from ports 4 and 5 of valve 134 fed directly to ports 5 and 6 of valve 133, through column 132 and to waste.

Alternatively, one or both columns may be bypassed by the sample altogether. For example, sample from valve 151 may bypass column 131 by switching valve 134 to state 1, which shunts the sample through ports (1), (2), (3) and (4) of valve 134 and into port (5) and (6) of valve 133 (state 1). From there, the sample feeds directly into column 132. Similarly, the sample may feed through column 131 as described above and exit column 131 via ports (5) and (4) (state 2) of valve 134, ports (5) and (4) of valve 133 (state 2) and then to the detector 136. The sample may bypass both columns by operating valve 134 in state 1 and valve 133 in state 2.

As illustrated, the output of whichever column is in the fluid path passes from port (4) of valve 133 past an absorbance detector 136 to port (1) of an output valve 137 similar to valves 151, 133 and 134. This valve (i.e., 137) allows one to pass the sample through the pH and conductivity sensors. When bypassing pH and conductivity sensors, State 1 of this valve connects the column output to port (2) and to a fraction collector. In this state, a sample injected at port (4) passes via port (3) through a pH/conductivity sensor 138 to port (6), thence to port (5) and to a waste vessel. A sample injected along this path maybe used to calibrate sensors, such as a pH sensor and a conductivity sensor.

When using the pH/conductivity sensors, valve 137 is switched to State 2 so the column output entering port (1) is passed via port (6) to the sensor 138, then via port (3) to port (2) to the collection system 139. The collection system may include either a single vessel for collecting single fractions from successive runs, or may include an automated system for receiving different successive samples in separate receiving vessels.

In yet another embodiment of the invention, a defined, but limited volume of a feed solution containing at least one target solute in admixture with other solutes is passed into first and second sample-holding loops which are in-line with each other and holding approximately equal volumes of the sample. Once the feed solution has filled these loops, the feed from the first loop is diverted into and through a matrix comprising binding sites specific to the target solute that are in excess of the molecules of target solute contained in the limited sample volume.

Figure 4B:
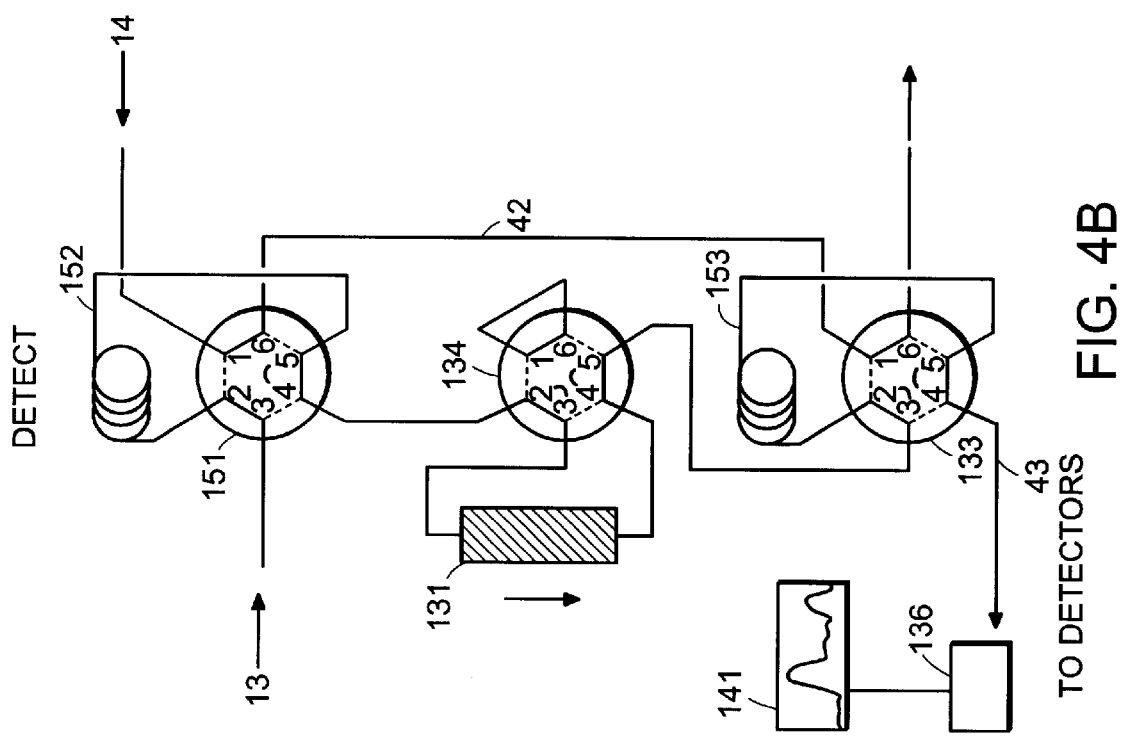
FIG. 4 is an illustration of an embodiment of the invention.
Figure 4A:
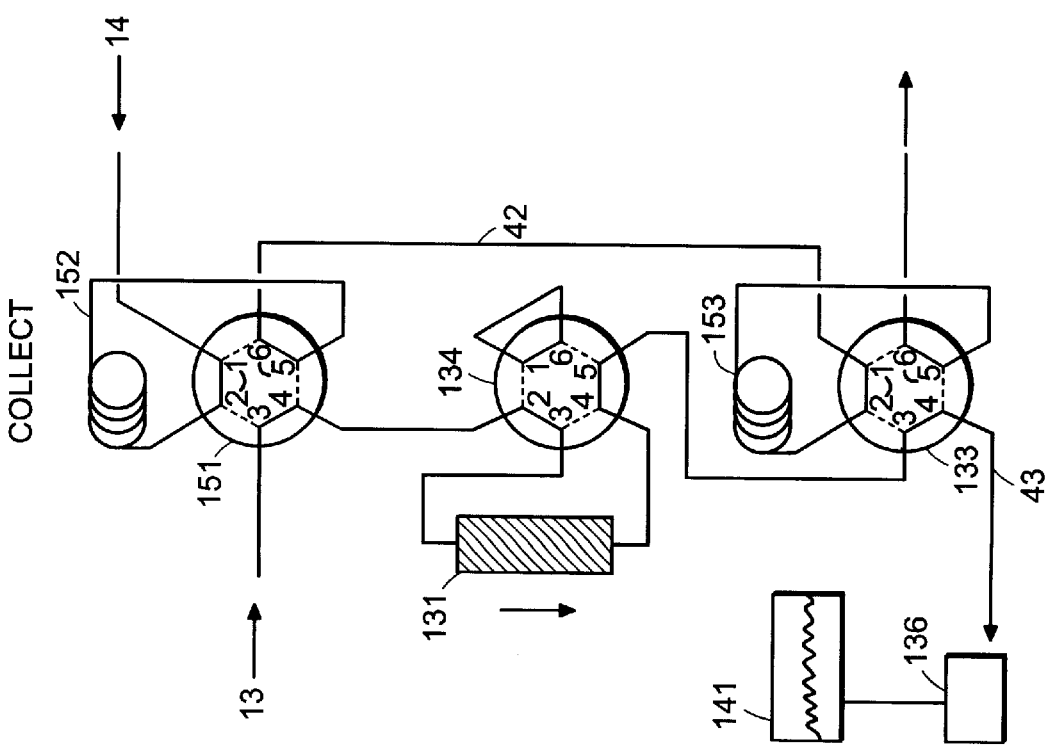

FIG. 4 illustrates this embodiment, which includes at least two multiport valves, at least one column, and one detector. The multiport valves may contain any number of ports; in FIG. 4, the valves include 6 ports. Each valve may be operated in one of two possible states, as described above. For collection of the sample, as show in FIG. 4(a), sample input 14 feeds the sample into valve 151 via port 1 to port 2, into sample loop 152, via ports 5 and 6 of valve 151 into line 42, and into sample loop 153 via ports 1 and 2 of valve 133, where it is held during switching of the valves. For sample detection, valve 151 is then switched to State 2, as shown in FIG. 4(b). Sample contained within loop 152 is then pumped via ports 5 and 4 of valve 151 and ports 2 and 3 of valve 134 to column 131, where the analyte or target solute is selectively adsorbed. The sample then exits column 131 and is fed via ports 4 and 5 of valve 134 to port 3 of valve 133. Valve 133 is now switched to State 2 such that ports 3 and 2 are interconnected and adsorbed sample from column 131 pushes the non-adsorbed sample contained in loop 153 through loop 153 and ports 5 and 4 via line 43 to detector 136. The adsorbed sample from column 131 follows the non-adsorbed sample through loop 153 to detector 136. The results are displayed via display 141.

Display of the detector readings will reveal a peak representing a high concentration of the original non-adsorbed sample followed by a second peak which is smaller than the first peak proportional to the amount of target solute removed by column 131. The second peak represents the impurities remaining in the sample after adsorption. If desired, the target solute may then be eluted and detected as described above.

The system may be regenerated by eluting and washing the column using a pump and buffers supplied, e.g., via ports 3 and 4 (state 1) of valve 151, ports 2 and 3 (state 2) of valve 134, and ports 3 and 4 (state 1) (or ports 3 and 2 ) to loop 153, and to ports 5 and 4 of valve 133.

In addition to monitoring the presence, quantity, and purity of a given product, a process stream from a preparative procedure and containing a continuously changing concentration of target solute can be continuously monitored such that a given detection signal, e.g., above a baseline, can trigger a valve switch to send sample through the column. Or, for example, detection of a product of given purity can trigger the collection of fractions, and detection of a fall in product concentration or purity below a defined level can trigger a signal for the fraction collector to discontinue.

The apparatus described in FIG. 4 will be useful for the following method. A defined, but limited volume of a sample solution containing a target solute is taken for quick analysis of the concentration of the target solute and impurities present in the solution. The method, for assay of a solution which contains one or more solute impurities and at least one target solute, may include the steps of: diverting a sample aliquot, i.e., a known volume, from a process stream into a sample feed line, passing a portion of the sample aliquot through a matrix having binding sites specific for at least one target solute to produce an effluent, substantially free of the target solute, obtaining a first data point representative of the concentration of impurities in the sample effluent and a second data point representative of the additive concentration of solutes in the sample, and determining the difference between the first and second data points, the difference being proportional to the concentration of the target solute in the sample aliquot. A "data point" may refer to either the height of or the area underneath a given peak, and "substantially free" means at least 95% free of the target solute.

The first and second data points may be obtained using substantially (i.e., >90%) equal portions of the sample aliquot, or if the aliquot portions are not equal, an internal standard of known concentration may be used to relate the first and second data points to each other, e.g., a protein of known concentration which does not bind to the column.

The process stream may be analyzed at selected times during the process, e.g., plural serial samples may be diverted from the process stream. The process stream may be produced by any preparative purification process, which may encompass, but is not limited to, purification of any antigen to which an antibody can be made, e.g., a protein, a steroid, an antibiotic, or a nucleic acid. As described in detail herein, the process stream may be produced by a preparative chromatography process, e.g., during relatively large scale preparation of a target protein.

Control of Process Steps

During the aforesaid course of operation, a central processing or control unit 142 maintains a unified time base and provides control signals along lines 144 to the different control valves and mixing valves to achieve the desired fluid make-up, sequence of operation, solvent flow and separation conditions. Processor 142 also receives electrical indications along lines 146 from the various output detection/sensing units, such as the UV absorbance detector 136, and the pH and conductivity sensors in output sensor 138.

In the preferred embodiment of the invention shown in FIG. 1, the processing unit 142 is connected in a user interface system which includes the keyboard for program/data entry, the display and mouse, and the printer for printing out data. Other conventional hardware elements such as disk memory or semiconductor RAM or ROM units, while not shown, are included in unit 142 for operation of the processor as described more fully below.

In accordance with one aspect of the invention, the control system not only controls the operation of valves for one separation run, but allows the entry of program data to automatically effect plural successive runs with the same or successive different solvents, and provides the desired mix of solvents, including a gradient mixture for the elution portion of a run.

In accordance with another aspect of the invention, the control program implements an interactive feedback loop, wherein output parameters of one run or set of runs are stored and processed to determine environmental conditions for a subsequent run.

Figure 6:
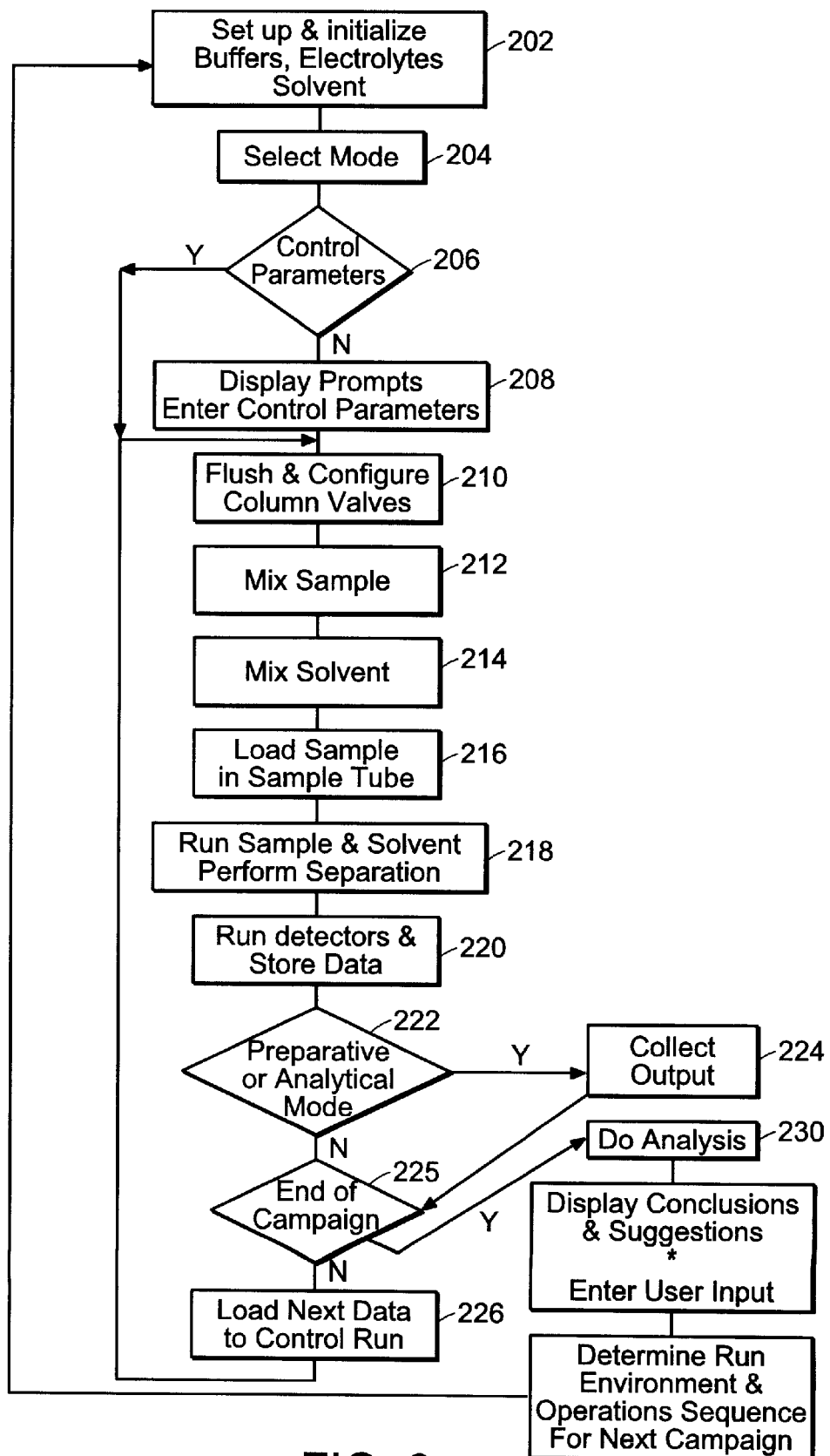
FIG. 6 is a flow chart showing CPU operation sequencing in a representative operating cycle of the embodiments of FIGS. 4–6.

FIG. 6 best illustrates program steps taken to control the apparatus. FIG. 6 shows an operational chart 200 of the functions controlled by the microprocessor during a representative process using a single column. It will be understood that certain aspects of the system may be fixed, e.g., the presence of the multiport valves, the particular mixing valves, solvent pump and sample injection pump, and several basic output sensors. Other elements, such as the sample buffers, solvent reservoirs, and size and type of chromatography columns may be changed for each use, or even between runs which are part of the same sequence or "campaign" of runs.

At a first state 202, the system is set up and initialized to run its control programs with the particular sensors, solvents, columns and buffers which have been selected for the separations, or the series of separation experiments, which are to be performed. This entails entering the values of global parameters such as column size and type, size of sample loop, identity or properties of solvents attached to each of the six mixing valve channels, identity of each output sensor, and the like. That is, the configuration of the instrument, the column, the solvents and the sample are specified.

In addition, certain default instructions for the control program may be entered, such as the default flow rate, whether certain output sensors are to by bypassed, and which steps of the equilibration, sample loading, wash, elution and regeneration should be performed, as discussed more fully below.

For operation, a mode is selected at 204, e.g., for routine execution of an analytical or preparatory protocol (i.e., a developed protocol) or carrying out method development runs (i.e., a process to develop a protocol). If a preparatory mode is selected, one specified separation method is repeatedly run to separate a number of identical samples, which are collected at the output. In this mode, at least one output sensor may be used to signal when the desired fraction has reached the output, so the controller may activate a valve to pass the output to a collecting vessel. In addition, data from the output detector is stored as a record for the run.

If an analytic mode is selected, the output proceeds to the output detectors and a record of the detected properties at each time is created; no fractions are collected. In either mode, the separation parameters are changed for each run. At 206, 208 a check is made whether a separation method has been fully specified or requires additional instructions, and, when a complete set of control instructions has been specified,the process proceeds to execute one separation run. This involves mixing the buffer and sample, mixing the solvent, configuring the columns, loading the sample tube and injecting the sample, and running the sample and solvent through the separation columns. These steps, indicated at 210, 212, 214, 216 and 218 are shown in a schematic and abbreviated representation; in fact, different subloops of steps 212, 214 and 218 will be repeated in successive stages to equilibrate, wash, elute or regenerate the columns in forward or reverse directions during one complete run.

After the separation has been run and the data collected and stored at step 220, the processing branches at step 222, proceeding to collect the designated fraction at 224 if operating in a preparatory method, and repeating an identified run until the specified multiplicity of samples have been separated.

According to a principal aspect of the present invention, the control software includes method-generation software which causes the separation apparatus to perform an experimental "campaign". This is a sequence of methods which are performed successively while varying a parameter each time a method is run. For example,the apparatus may run a series of twenty one separations in which the pH of the solvent is varied in increments of (0.1) between pH 5.0 and 7.0, or in which the molar concentration of sodium chloride varies in steps of (0.1). After running one method in this mode, a determination is made whether such a campaign has ended, and if not, the parameters for the next run are loaded 226 and a new run starting at step 210 or 212, as appropriate, is run.

According to another principal aspect of the invention, the recorded data from one run or a complete campaign proceeds to an analysis module 230. This module operates on several levels.

At a first level, the module includes numerical analysis and spreadsheet processing programs, so that it may process all recorded data and print out or display charts and graphs depicting the output characteristics as functions of the various input parameters exercised during the run or campaign.

At a second level, the module includes analysis software which facilitates or even automates the development of a separation method. This software may include an artificial intelligence program of the "expert system" type. For example, the second level of analysis may include stored templates which recognize certain classes of proteins by a characteristic output behavior when subjected to a pressure-variation or a pH variation campaign in a particular separation medium, or output templates which otherwise recognize possible patterns. Such program preferably is keyed to a module of program entry or selection software, which causes the monitor 143 to display prompts that guide an operator in selecting a method or series of steps which optimize the separation of the substance of interest. Thus, for example, when the approximate molecular weight and certain presenting groups have been identified from the transport speed and the separation dynamics on a particular medium, the program might suggest a campaign of varying pH in a different column which has proven effective for a group of proteins of the identified type. Thus, the analysis program at this level includes templates for the recognition of salient protein properties, and includes tables or prescriptive messages keyed to the templates. At an elementary level, the analysis program may also provide a series of several unrelated methods which quickly determine an appropriate separation medium, or detect whether the substance of interest is passing ahead of other fractions or should be separated as a column residue by elution, and if so whether an isocratic or a gradient solvent should be employed for the elution step.

In this manner, it will be seen that the control program of the present apparatus eliminates many of the manual or piecemeal preparatory steps required in the prior art for developing or optimizing a protein separation method, and reduces the time required for such steps, including the thought processes involved in the selection of such steps, to less than the time required to run a separation in one column. Thus, as a solvent is flowed through the columns, the processes of column regeneration, selecting the parameters for the next run, and mixing the samples and solvents for the next run all proceed simultaneously. A further advantage of such operation is that a higher degree of uniformity and freshness of all fluid preparations is achieved, leading to greater accuracy of correlation with the output characteristics detected by the output sensors.

Chromatographic Matrices

One can increase chromatographic throughput in the chromatography system of the invention by using a matrix comprising small porous particles having a relatively large pore diameter, so that convective flow can be induced through, as well as around, the particles. This type of chromatography is referred to as Perfusive Chromatography and is described in copending application Ser. No. 376,885, filed Jul. 6, 1989, now U.S. Pat. No. 5,019,220 the disclosure of which is incorporated herein by reference. Perfusive chromatographic techniques permit high speed, high capacity, high resolution separation. Perfusive matrices may be purchased from PerSeptive Biosystems, Inc. of Cambridge, Mass.

Perfusive matrices comprise rigid, porous, high surface area materials such as particles which may be of the same mean diameter as are employed in conventional chromatography matrices. The geometry of perfusive matrices are configured to allow convective fluid transfer both within and between the particles. Typically, 10–20 μm diameter particles of perfusive matrices have throughpores of relatively large mean diameter (e.g., 6,000 to 8,000 A) and a high surface area network of internal, blind subpores of smaller mean diameter (500 to 1500 A) within the throughpores. The interactive surface elements can be immobilized on all available surface areas, including within the throughpores and the subpores.

Perfusive matrices are characterized by a relatively small ratio of the mean diameters of the interparticle flow paths to the intraparticle throughpores, thereby permitting intraparticle convective flow at accessible fluid flow velocities. The resulting network limits the diffusional path lengths within the particles so that mass transfer within the particle pores is governed by convection rather than diffusion over a large range of high flow rates. Where the perfusive matrix comprises packed particles, the diameter of the particles determines the mean diameter of the interparticle spaces in a packed bed. The ratio of the mean particle diameter to the mean diameter of the intraparticle throughpores may be less than 70, most preferably less than 50. Preferred subpore diameters are within the range of about 300–700 A°. In addition the low ratio (and correspondingly larger intraparticle pore size) substantially reduces particle pore effects. Preferred ratios of convective flow velocities through the interparticle and intraparticle pores are between about 10:1 to 100:1.

Examples of chromatographic matrices useful according to the invention are matrices having multiple positive charges on their surface, e.g., a strong anion exchange coated sorbent, as described in U.S. Ser. No. 07/565,628, now abandoned filed Aug. 10, 1990, assigned to the same assignee and hereby incorporated by reference; chromatographic matrices having an adsorbed coating on the hydrophobic surface of the matrix beads which produces a continuous hydrophilic film. The adsorbed compounds may contain hydroxyl, epoxy, halide, or other reactive side groups, as described in U.S. Ser. No. 07/469,956, Jan. 25, 1990, issued on Jul. 9, 1991, patent no. 5,030,352, assigned to the same assignee and hereby incorporated by reference; and matrices having enzymes immobilized thereto, described in U.S. Ser. No. 07/469,956, filed Jan. 25, 1990, assigned to the same assignee and hereby incorporated by references.

Alternatively, a non-porous chromatography matrix having high surface area may be used. A non-porous particle system contains tortuous channels which are formed, as are diffusion bound systems, by the interstitial space among the particles. This may also be obtained from Glycotech, Inc., West Haven, Conn. Lower performance matrices, e.g., conventional HPLC supports or low pressure liquid chromatography supports may also be used in certain embodiments of the invention.

Chromatographic Procedures

The chromatography system of the invention may be used for a preparative or analytic procedure in which the ultimate goal is to separate one or more components of a protein mixture. FIGS. 7–11 show representative chromatograms resulting from chromatographing procedures using the apparatus of the invention. For example, chromatographic procedures may be used according to the invention which exploit the benefits of high speed chromatographic techniques to allow, e.g., identification of a peak in a chromatogram (FIG. 8); detection of trace solute contaminants in a solution that contains a major amount of a dissolved product (FIG. 7); real time monitoring of solute concentration in a process mixture (FIG. 9); production of a profile of a mixture representative of the nature and relative concentration of structured variants of a given solute ("fingerprint" or "breakthrough" analysis) (FIG. 10); rapid determination of the presence and location of a solute in a chromatography effluent during, e.g., any step of a preparative procedure (FIG. 11); and rapid assessment of the success of a purification or separation protocol. Several representative chromatography procedures are described in the following examples. However, the invention broadly encompasses other purification or analytic schemes which are not described in detail herein.

EXAMPLE 1

The chromatography system of the invention may be used to detect a trace solute in a solution containing a major amount of a dissolved product. Trace solute detection is described in U.S. Ser. No. 07/721,192, now abandoned filed Jun. 26, 1991, assigned to the same assignee and hereby incorporated by reference. The trace solute detection procedure may, for example, involve flowing the solution through means for extracting the product to produce an effluent flow substantially free of the product but containing the remaining trace solute or solutes, flowing the effluent through a trace solute adsorber to progressively accumulate therein the trace solutes, and eluting the accumulated trace solutes from the adsorber to produce an eluent fraction containing a detectable quantity of the trace solute.

This trace solute detection method may be performed according to the invention as follows. Referring to FIG. 3, a sample containing a mixture of product and trace solute impurities is provided from any one of reservoirs 117a–d via mixing valve 116 and along line 118 into valve 151 via port (4) of the valve. With valve 151 in state 1, sample is pumped via port (4) to port (5) and tube 152. Sample remains in tube 152 while the valve is turned to State 2 and solvent is pumped into the system via line 114 and port (1). Solvent is pumped from port (1) to port (2), pushing the sample from tube 152 to ports (5) and (6) and then into a first column 131 via ports (1) and (6) of valve 134. The sample is then transported to column 131, which is capable of selectively binding the sample product component, and thus extracting it from the sample. Column 131 may contain, for example, an immunoglobulin-bound matrix, where the immunoglobulin is specific for the major target component of the samples.

The capacity of column 131 is at least large enough to extract virtually all of the product from the sample solution, and preferably is far larger. The effluent stream from column 131 containing the trace solute impurities then is passed through ports (5) and (4) of valve 134 to ports (5) and (6) of valve 133 and into, a second column 132 that is capable of adsorbing the trace impurities, and thus extracting them from the sample solution. A relatively large volume of sample and thus of product-extracted effluent is passed over the second column, which adsorbs the trace solutes from the sample solution, typically nonselectively, and thus accumulates trace solute contaminants. Effluent from second column 132 exits through detector 136 to assure that it contains no unadsorbed contaminants, and then to waste 140. The trace solutes are then eluted from the second column 132 along the same path through the detector 136 to produce an output which describes, for example, the temporal and/or spatial sequence of the trace impurities exiting the second system. Where the trace solutes are protein, the second column 132 may be any protein-binding matrix; reverse phase, hydrophobic interaction, ion exchange, etc., and detection may proceed via a conventional detector, e.g., one which measures ultraviolet absorbance through a film of fluid. Trace solutes other than protein may be detected by appropriate conventional means.

Figure 12A:
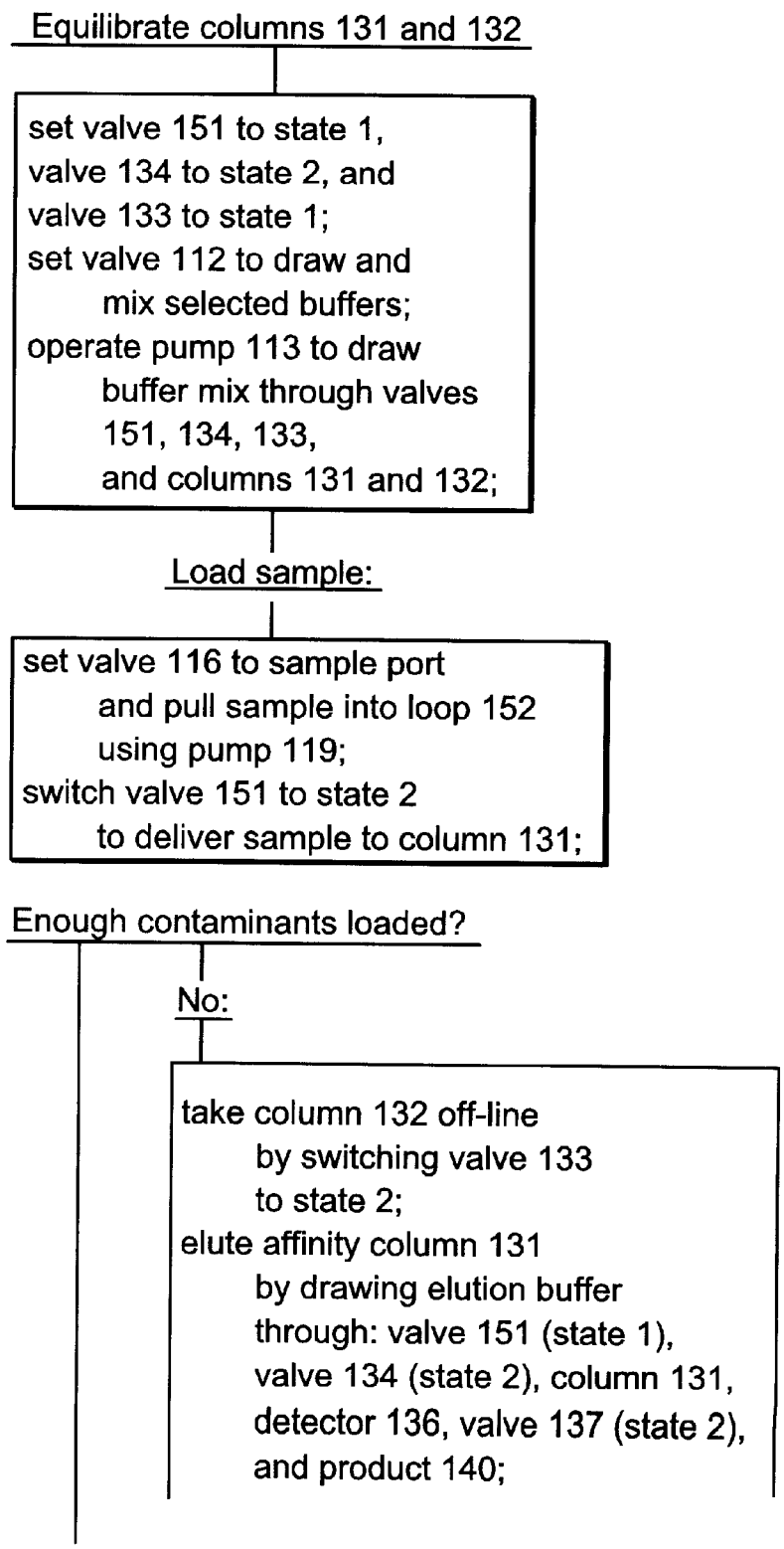
FIGS. 12(*a*) and (*b*) is a flow chart for operating the apparatus of the invention to detect trace contaminants in a sample.
Figure 12B:
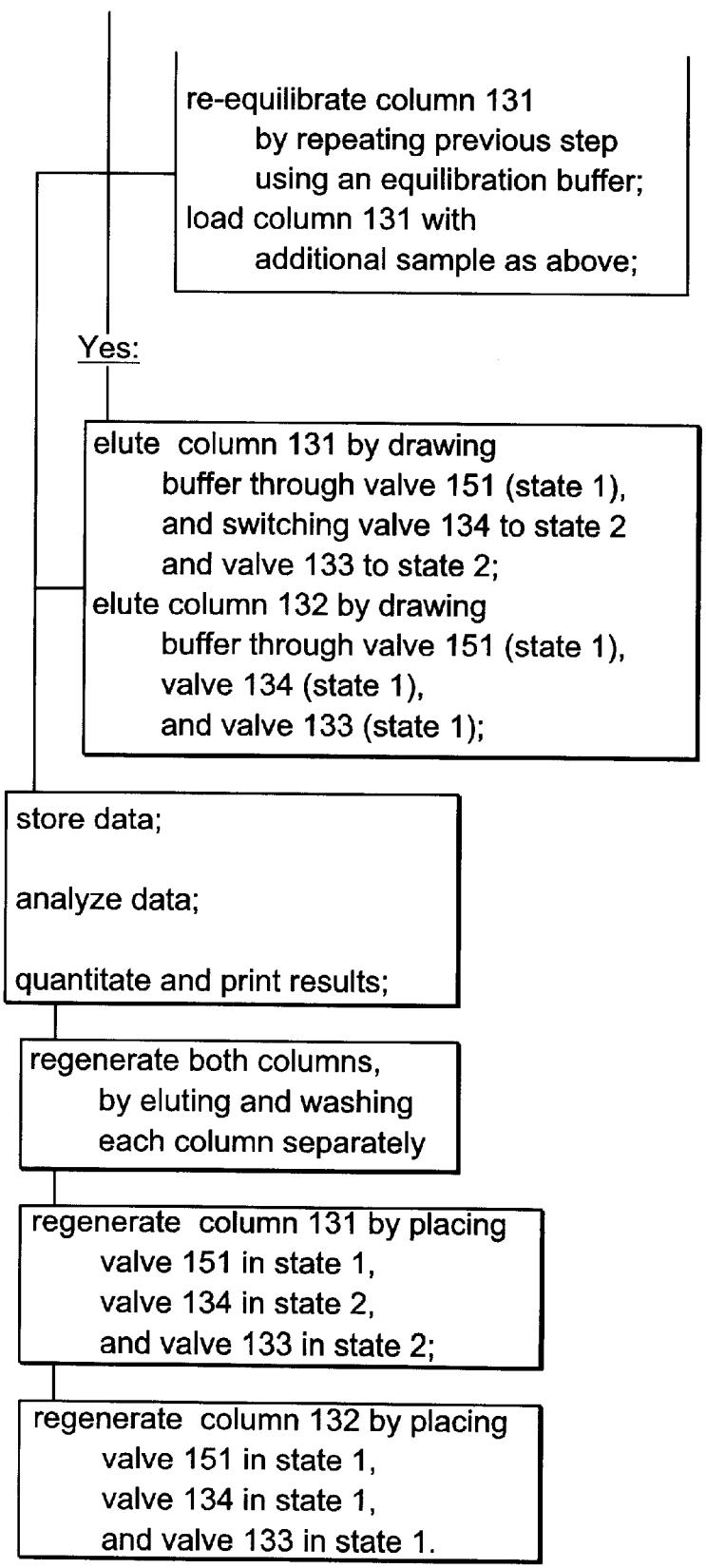

The very high sensitivity of the apparatus is a consequence of the ability of the second system to concentrate the impurities by: (1) accumulating them as a relatively large volume of product-extracted sample is flowed through, and (2) to release the impurities in a relatively very small volume of eluent. Thus, for example, 100 ml of sample containing $10^{-3}$ g/ml product and $10^{-12}$ g/ml impurities can be passed through the apparatus. The product (0.1 g) is extracted in first column 131 and the impurities ($10^{-10}$ g) accumulated in second column 132. Next, the impurities in second column 132 are eluted with, e.g., 10 microliters of eluent, to produce an effluent sent to detector 136 having a detectable concentration of $10^{-10}$ g/$10^{-5}$ liters or $10^{-5}$ g/l. Product extracted in first column 131 then may be recovered by passing an eluting solution from port (6) of valve 134, into column 131, and out of the system via valves 134 and 133 after bypassing column 132, as described above. FIG. 12 shows a flow chart of steps that may be taken to perform the procedure described above.

For this embodiment of the invention, one, two or all three of multi-port valves 151, 133 and 134 may be used. Multi-port valve 151 may be used to provide, alternatively, sample through port (4), eluant through port (1), or equilibrating buffer through port (1) to the first column 131, to provide all necessary flow streams. Valves 133 and 134 may be adjusted to permit sample effluent or buffer exiting column 131 to be flowed into column 132, to introduce an eluant into column 132, to permit eluant from column 131 to be diverted to waste in preparation for the next assay, or to collect product. Valves 134 and 133 may also be configured so as to permit passage of effluent or eluant from second system column 132 to waste or to detector 136. Valve position for all multi-port valves may be under either manual or computer control, and fluid delivery may be driven by one or more metering pumps (not shown). The multi-port valves further may include "stream splitters" or other means for reducing and/or directing only the desired flow rate to the first and second columns.

The sample path in this embodiment of the invention may be envisioned as follows. The sample is loaded, e.g., by a metering pump, into first column extractor 131 via valves 151, 134, and 133. As the sample flows through column 131, the sample product component is retained in column 131 and the effluent flows out of first column 131 via valve 134 into second column 132. Trace solutes that are present in the effluent sample are retained by second column 132. Once all of the effluent is flowed through second column 132, the multi-port valve 134 may be turned to allow washing of column 132, after bypassing column 131, via a wash solution which flows into column 132 from port (6). The wash may exit column 132 via port (1) of valve 133. The trace solutes may be eluted from column 132 using an elution buffer held in one of reservoirs 111a–f; the elution buffer may also be delivered to column 132 via port (6) of valve 133. The relatively small elution volume containing the trace solutes will pass via valve 133 into detector 136. Detection may occur by any convenient assay e.g., if UV absorbance is used, an absorbance spectrum may be generated which shows the presence and amount of one or more trace solutes present in the eluted sample separated by the chromatographic means of column 132. If the extracted product is to be recovered from first column 131, column 131 may be washed using a wash solution delivered to column 131 via port (6), of valve 134, and an eluant may also be delivered to column 131 via port (1) of valve 151. The eluted product sample may be recovered from column 131 via valves 133 and 134, detector 136, and fraction collector 149, once the multi-port valves are turned to the proper position. Any or all of the above steps may be automated by computer instructions.

Figure 7:
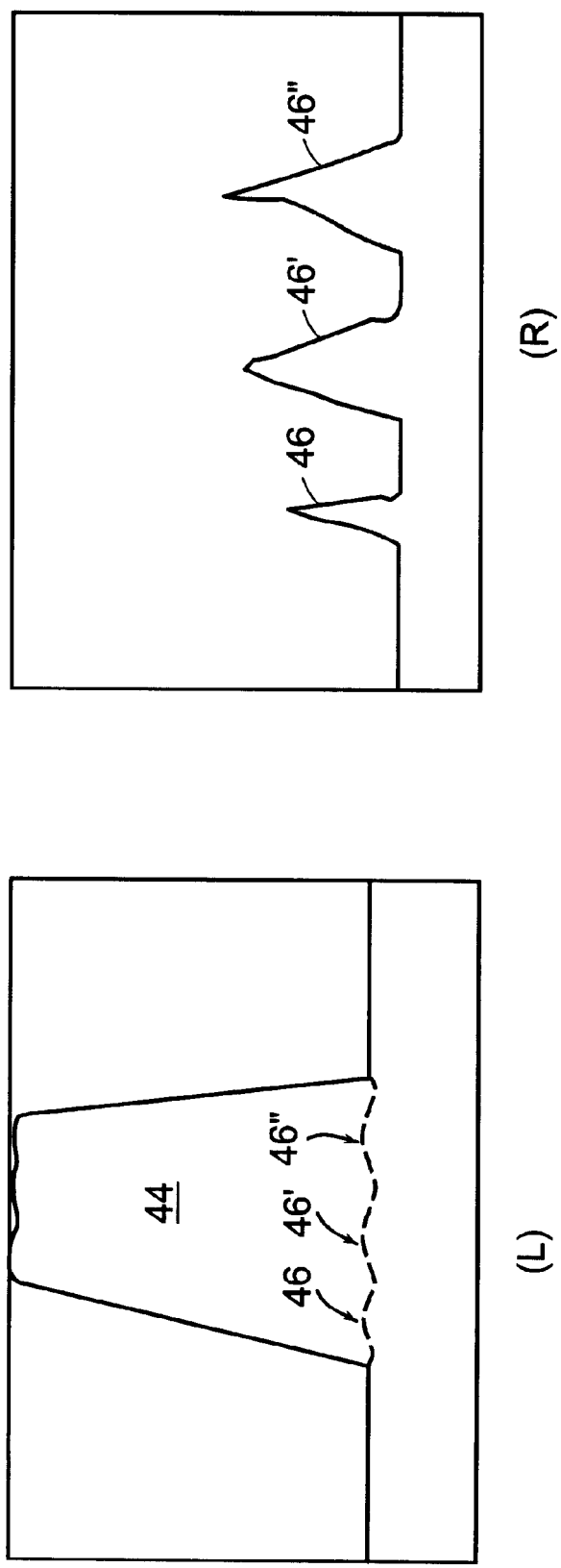
FIGS. 7–9, 10(*a*) and (*b*) and 11(*a*) and (*b*) show representative chromatograms of chromatography procedures utilizing the apparatus of the invention.
Figure 8A:
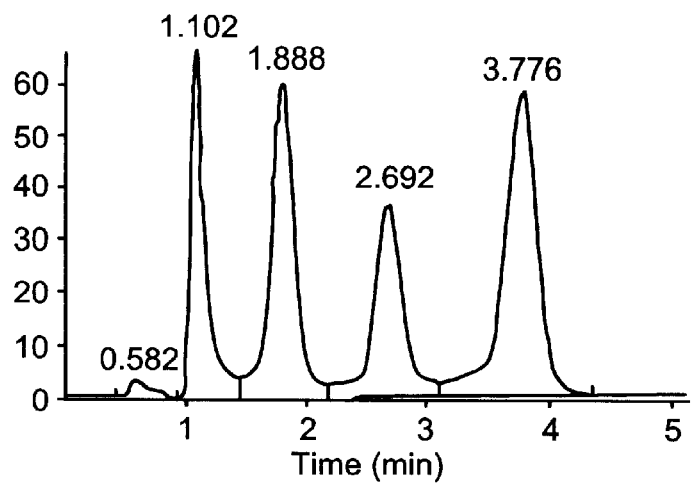
Figure 8B:
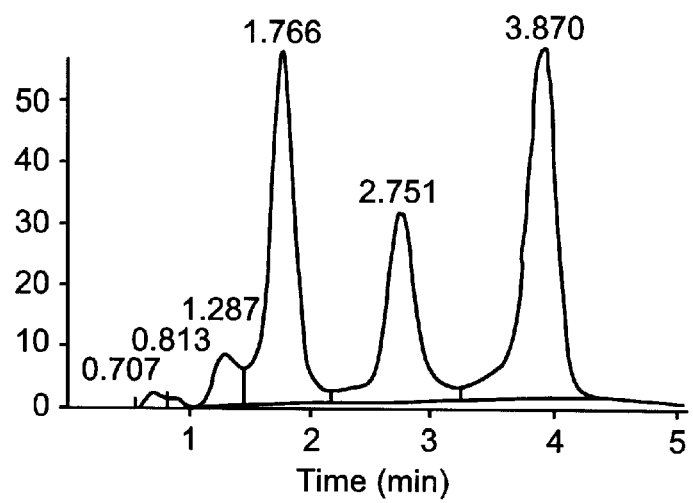
Figure 8C:
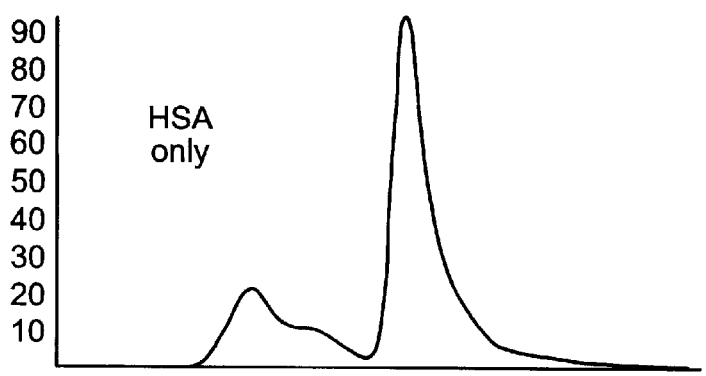

As part of a product assessment or product monitoring system, the method and apparatus of the invention is useful in identifying the presence of trace contaminants that copurify with the product of interest. FIG. 7 shows chromatograms representative of data from a trace solute detection procedure. The chromatogram to the left (L) shows the sample profile before removal of the major product 44 of the sample; to the right (R) is a chromatogram after passage of the sample through column 131 to remove the major product and through column 132 to collect the trace solutes 46, 46', 46". FIG. 12 shows a flow diagram of an ordered sequence of steps which may be taken to detect trace impurities. Provided that the first system selectively extracts essentially all of the product of interest from the fluid phase without significantly affecting the quantity or composition of the trace impurities in the sample mixture, the presence and concentration of trace amounts of impurities in the sample can be detected according to the invention.

Among the key features of the invention which make it useful as part of a product and/or process monitoring protocol are the speed, quality, and reliability of solute trace contaminant detection. While the method and apparatus theoretically could be implemented using conventional liquid chromatography, e.g., HPLC, for the first and second columns, for practical use, rapid fluid transfer must occur through both columns in the apparatus, and there must be no significant loss of resolution between the first effluent stream and the eluant.

EXAMPLE 2

The chromatography system and apparatus of the invention may be used to rapidly identify the presence and location of a preselected solute or subset of solutes in an effluent stream. This method is described in U.S. Ser. No. 672,872, now abandonded filed Mar. 28, 1991, assigned to the same assignee and hereby incorporated by reference. The method and apparatus of the invention are particularly useful as part of monitoring system for detecting the presence and/or absence of an absorbance peak during a preparative protocol.

To identify a solute of interest in an effluent stream, the mixture is first passed through a column capable of separating the components in the mixture (solutes) so that they are separated temporally and spacially to some degree as they exit the column in a fluid phase (effluent stream). The first column may contain a liquid chromatography matrix. The effluent stream from this first solute separation column (referred to herein as "first effluent stream"), then is passed through a detector to produce a first output describing the sequence of the solutes exiting the column. Identification of a particular solute of interest within this sequence of solutes is determined by passing this first effluent stream through a second column capable of selectively extracting the solute of interest from the fluid phase. Except for its ability to extract the solute of interest, this second column should be substantially inert, so that the sequence of solutes is essentially unaltered as the fluid phase passes through the second column, except that it will be substantially depleted in the component of interest. Preferably, the selective extraction occurs by some form of specific binding interactions between the matrix and the solute of interest. Particularly useful selective extraction columns include use of immunoadsorbents and immunoaffinity matrices.

The effluent stream exiting the second column then is passed through a detector to produce a second output which describes the sequence of the components existing the second column. Because the second column selectively extracts the component of interest without significantly altering the temporal and/or spacial arrangement of the other solutes in the effluent stream, the difference between the first and second outputs can be used to determine the location in the effluent stream of the product of interest. Thus, the component of interest may be missing or depleted in the second output. Accordingly, a comparison of the two outputs will identify the location of the solute of interest in the first effluent stream.

The detectors used to detect column output may be any means for molecule detection commonly used in the art. Currently preferred detectors include apparatus capable of monitoring the U.V. absorbance of a liquid, such as a spectrophotometer. In addition, both the first and second outputs may be produced by a single detector or alternatively, by separate detectors. Similarly, the first and second outputs may be compared visually or electronically. Electronic comparison may include subtraction of the second output from the first output to produce a third output presenting only the presence and location of the component of interest in the first effluent stream. The detector also may comprise means for calculating and displaying the concentration of the solute of interest in the first effluent stream. In addition, the component of interest bound to the second column matrix subsequently may be eluted, detected and quantitated as a means of confirming the data generated by subtraction. This method, when used according to the invention, may be integrated into an automated purification or other preparative system, to act as a product and/or process monitor, and the various steps involved in performing the method of the invention placed under computer control.

This method may also be used to identify multiple components in an effluent stream, by passing different samples of the first effluent stream through a second column capable of selectively extracting different solutes of interest and comparing the outputs from these systems with the first output; and to assess the purity of a solute of interest. Because the second column is designed to selectively extract the solute of interest from the first effluent stream, the presence of any contaminants that coelute with the solute of interest in the first effluent stream will be indicated in the second effluent stream. For example, in FIG. 8, three chromatograms represent (a) the sample after having been passed through a first column capable of separating components of the sample into four peaks; (b) the sample after having been passed over a second column that selectively removes a solute (peak 1) from the effluent stream from the first column; and (c) the solute (peak 1) after elution from the second column.

This method may also be used as part of an on-line process monitoring system to assess process conditions in real time, with the information generated used to alter conditions as needed to optimize production. For example, coeluting solutes identified by overlapping peaks in monitoring output on-line may be separated by altering particular process conditions such as, for example, a buffer pH or the parameters of an elution gradient.

This method may be understood in the context of the apparatus of the present invention by referring to the schematic representation of the embodiment of the invention depicted in FIG. 3. A sample containing the mixture to be separated is provided to a first column 131 capable of partitioning the components of the mixtures (solutes). The effluent stream from this column 131 containing the separated solutes then is passed through ports (5) and (4) of valve 134 and ports (5) and (4) of valve 133 directly to detector 136 to produce a first output which describes the temporal and/or spacial sequence of the mixture components exiting the first column 131. The sample separation on column 131 is then repeated, but the sample is passed from column 131 directly to column 132 via ports (5) and (4) of valve 134 and ports (5) and (6) of valve 133. Column 132 is capable of selectively extracting a solute of interest from the first effluent stream. The temporal and spacial sequence of the solutes in the second effluent stream will be substantially identical to that of the first effluent stream, provided that the second column is of an appropriate geometry and is sufficiently inert such that all but the component of interest pass through the column without significant interaction or delay.

Figure 13A:
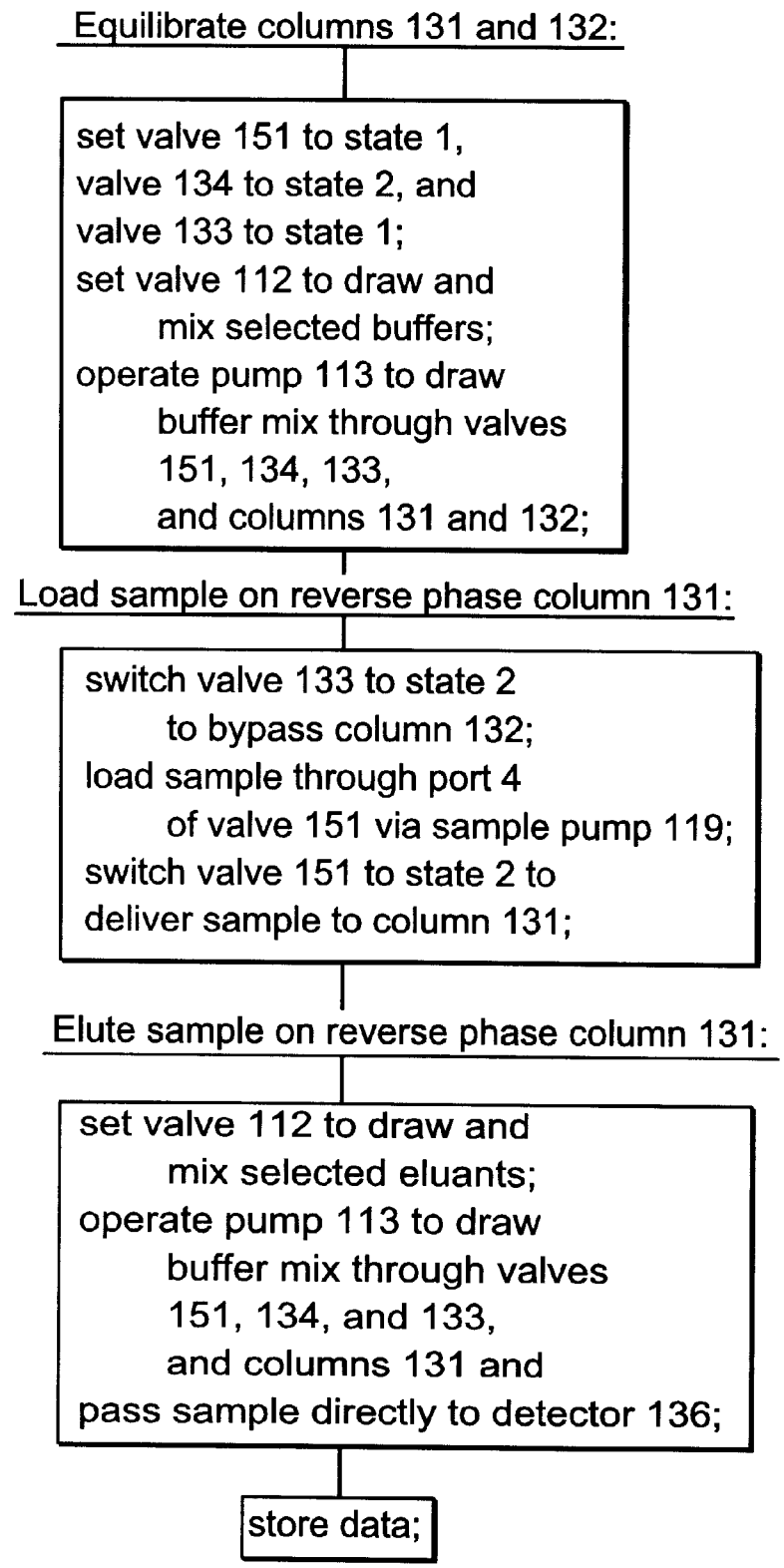
FIGS. 13(*a*) and (*b*) is a flow chart for operation of the apparatus and system of the invention to chromatograph a sample according to the invention.
Figure 16B:
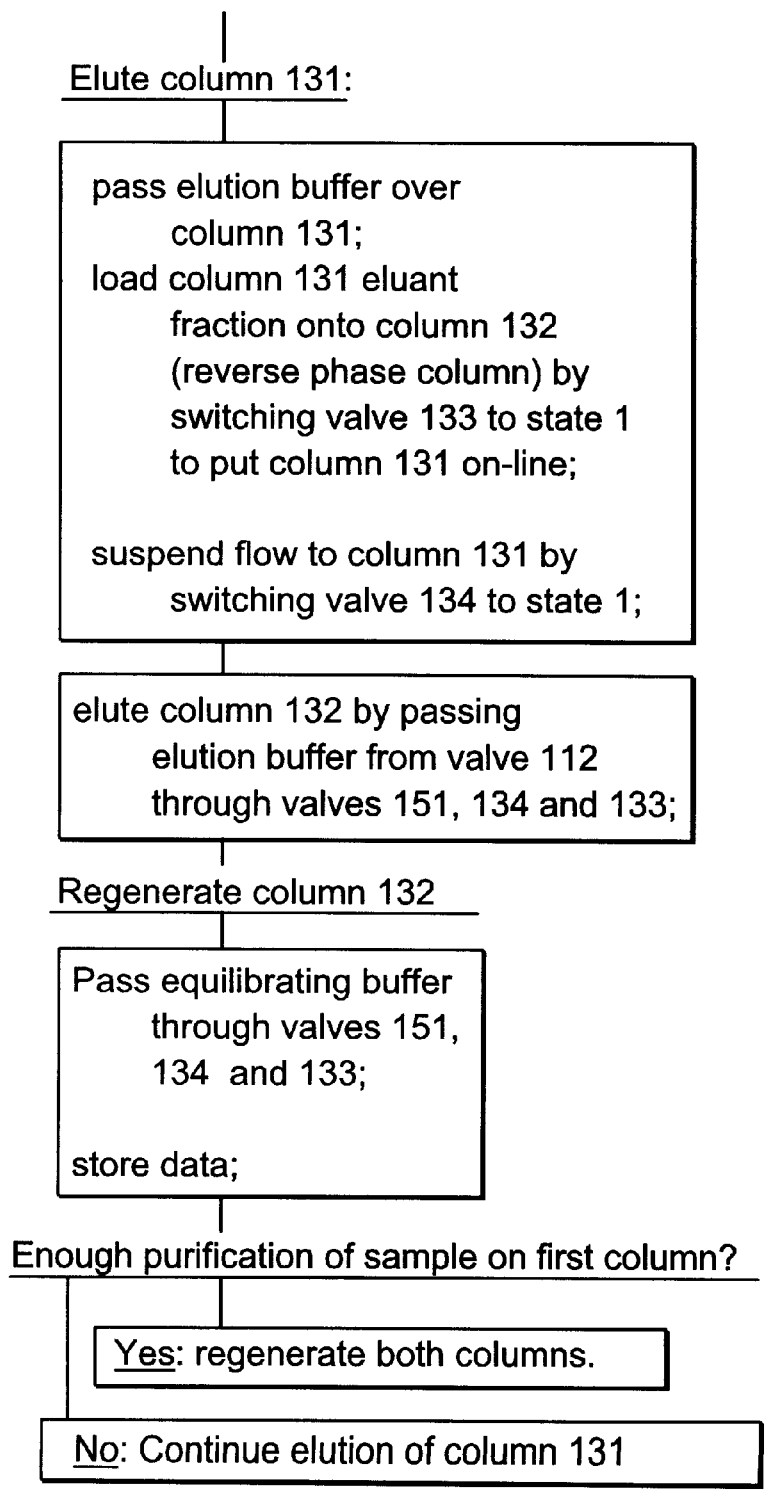
FIGS. 16(*a*) and (*b*) is a flow chart for operating the apparatus of the invention to perform a preparative/analytical run.

The effluent stream exiting the second column 132 then is passed again through detector 136 to produce a second output describing the temporal and/or spacial sequence of the solutes remaining in the effluent. The detector also may subtract the second output from the first output to produce a third output describing only the presence and position of the solute of interest in the first effluent stream. The detector also may have means for determining the concentration of the solute of interest in the first effluent stream, and means for displaying this data. Finally, the bound solute may be subsequently eluted from the second column, detected, and quantitated to confirm the subtraction data. Where the solute of interest is a protein, a typical detector is a conventional detector which measures U.V. absorbance through a film of fluid. FIG. 13 shows a flow chart of steps that may be taken to perform the procedure described above.

This method may be used as a monitoring system within a molecule preparation system, which may be automated. As above, multi-port sampling valve 151 may provide samples to the first column 131, as well as all necessary solvents or buffers, including washing solvents, eluting solvents, "running" solvents for electrophoresis systems, and recycling solvents to regenerate the system as needed between samplings. Similarly, multi-port sampling valve 133 provides fluids to the second system, including the first effluent stream and all necessary solvents. Valve position for both multi-port valves preferably is under computer control, and fluid delivery may be driven by a metering pump 113. As described above, the multi-port valves further may include "stream splitters" or other means for reducing and/or directing only the desired flow rate to the first and second columns. Valves 133, 134 at the exit of both the first and second columns direct the fluids exiting the columns to detector 136, or to waste or product collectors via valve 137. If desired, means also may be provided for recycling the detected samples.

As part of a process monitoring system, the method of this invention may be useful in assessing and/or developing a particular separation or purification protocol. For example, in an ion exchange chromatography system, variations in pH significantly affect solute separation. Using the chromatography system and apparatus of the present invention, one can rapidly assess the effect of various pH values on solute separation on-line, and alter appropriate conditions to optimize separation. This assessment can be performed rapidly using minute sample quantities. Accordingly, the method allows on-line production optimization without substantial loss of sample or time.

The method of this invention also may be useful in identifying the presence of contaminants that coelute with the solute of interest. Provided that the second column selectively extracts essentially all of the solute of interest from the fluid phase without significantly affecting the quantity or position of the remaining solutes in the sample mixture, the presence of a solute in the second output at the position generally occupied by the solute of interest can indicate the presence of a contaminant. Moreover, identification can be corroborated by eluting the solute of interest, quantifying it and comparing this value with that for the pertinent peaks in the first and second outputs.

Among the key features of this invention which make it useful as part of a product and/or process monitoring protocol are the speed, quality, and reliability of solute identification. This requires rapid fluid transfer through both columns in the apparatus, and no significant loss of resolution between the first and second effluent streams.

Resolution of partitioned solutes in a mixture is a function of both the affinity of the various solutes for the partitioning component (generally a matrix) and the theoretical plate height of the system. A "plate" in column chromatography can be considered to be the largest uniform zone able to accommodate a solute. The smaller the plate height of a column, the more discrete steps (higher plate number) a solute will encounter traveling through the matrix, providing better separation between similar components. Generally, the greater the matrix surface area-to-column volume ratio, the smaller the plate height and larger the plate number achievable. Column design generally focuses on designing the smallest matrix volume possible that provides a sufficient plate number to resolve components of interest. Smaller volumes increase the speed of fluid transfer through the system and reduce zone spreading. Preferred matrices are those composed of porous particles, as these provide a substantially greater surface area-to-volume ratio than a packed matrix of solid (non-porous) particles.

The equipment is designed to operate at high pressures because the dense packing of small beads creates a high resistance to liquid flow, which allows rapid fluid transfer. The densely packed particles create a large surface area-to-volume ratio which works well resolving small molecular weight solutes. However, conventional HPLC systems are substantially less successful when used to resolve large molecular weight solutes such as proteins. Flowthrough speed of large molecular weight solutes such as proteins through a conventional HPLC matrix becomes limiting, primarily because mass transfer within the particle pores becomes diffusive, as compared to the mass transfer between pores, which is convective. While one can increase flow rates at the expense of high pressure drops, this tends to reduce separation quality. Miniscule columns (microcolumns) may be used and analysis may be performed at heretofore unattainable speeds with no significant loss of resolution.

Perfusive matrices are currently preferred liquid chromatography matrices for both the first and second columns in this form of the invention. Perfusive matrices for use in the first column, designed to partition and resolve components of a mixture, may be derivatized as desired using conventional methods known to those of ordinary skill in the art, to create a particular chromatography system. For example, the matrix may partition solutes by size, or be derivatized to separate solutes by charge (e.g., act as ion or anion exchangers), by metal ion affinity, or by hydrophobicity or hydrophilicity. Other useful matrices include inorganic substances such as calcium phosphate (hydroxyapatite), bentonite, alumina, and titanium or zinc oxide gels.

As stated above, the second column should not significantly affect the position or concentration of the solutes remaining in solution. This means that the geometry of the system is important. The minimum volume that will adequately bind substantially all of the solute of interest should be used. In addition, non-specific binding must be minimized to prevent false negatives. Preferably, non-specific adsorption should be less that about 1 ng/10 ul. Accordingly, the binding surface or matrix should be substantially inert, capable of selectivity extracting the solute or solutes of interest, preferably quantitatively, without significantly altering the resolution of the solutes remaining in the effluent. If desired, non-specific binding may be further minimized in the second column by first coating the potential non-specific binding sites with a nonspecific molecule, before loading the sample. It will be understood by those skilled in the art that this "coat" molecule should bind sufficiently under elution conditions so as not to interfere with the output of the second effluent stream.

Currently preferred matrices for selectively extracting the solute of interest are those capable of specific binding interactions with the solute. Most preferably, these interactions are reversible, and the system may be regenerated by means of one or more recycling solvents capable of dissociating for the solute from the column, and preparing the system for another sample. Useful solute-specific sites include immunoadsorbents (e.g., antibodies) and other proteins capable of interacting specifically with the solute of interest. For example, one can envision the solute and solute-specific binding site comprising any ligand/enzyme combination, including hormones, toxins, lectins and their appropriate receptors. Where the solute of interest is an enzyme, the binding site may comprise a pseudo-substrate or an inhibitor. In general, the solute-specific binding site (solute-specific affinity sorbent) can be any immobilized ligand that demonstrates a bioaffinity for the given effluent of interest. The matrix surface may be derivatized so that the solute-specific binding site is bound irreversibly to the matrix surface. The bound solute then may be eluted and the column regenerated for subsequent samples. Alternatively, the solute-specific binding site may be attached non-covalently to the matrix surface. This allows the system to be adapted for use with different target solutes. One particular solute-specific binding site may be removed from the system by means of one or more recycling solvents, and a second binding site, specific for a second, different solute, then applied to the system. For example, protein A or protein G may be covalently bound to the matrix surface, allowing multiple, different solute-specific antibodies to be bound to the matrix in turn.

EXAMPLE 3

The chromatography system of the invention is also useful for rapid assay and characterization of therapeutic and other substances, based on what is described herein, and in U.S. Ser. No. 07/566,121, filed Aug. 10, 1990 and U.S. Ser.

No. 07/676,872, now abandonded filed Mar. 28, 1991, which are assigned to the same assignee and hereby incorporated by reference, as "subtractive chromatography". In accordance with the invention, a solution containing multiple solutes is passed through a column containing a matrix having binding sites specific for one or more target solutes. As used herein, "target solute" is broadly defined and encompasses any water soluble analyte but typically is a protein such as a protein produced by recombinant techniques. By analyzing the effluent flowing from the column, the presence and concentration or the profile of the structural variants of the target solute, i.e., similar molecules containing differences in amino acid sequence or glycosylation patterns, can be determined, thus providing two dimensional analysis of a sample fraction.

Accordingly, a feed solution containing at least one target solute, for example, a biologically active molecule such as a polypeptide, protein, polysacharride, or the like, in admixture with other solutes, is passed through a column matrix comprising binding sites specific for the target solute. As the feed solution passes through the matrix, the target solute will adsorb at the binding sites, thereby virtually eliminating any concentration of the target solute in the effluent. During this process, a limited amount of non-target solute may also non-specifically adsorb to the matrix. The effluent is monitored to determine its solute concentration. While this will entail monitoring the ultra-violet absorption of the effluent, which is proportional to concentration, it should be understood that any number of alternative monitoring methods can be used to the same effect. Any method which produces data related to the solute concentration of the effluent is suitable.

As the effluent begins to flow from the column, the concentration of contaminating or "non-target" solute(s) in the effluent will increase until the concentration of non-target solute in the effluent reaches an equilibrium level equal to the concentration of non-target solute in the feed. When graphed as the relationship between, for example, ultra-violet absorption and time, this stage of the assay procedure will result in an upturned slope or vertical line, depending on the nature of the matrix, which develops into a flat, horizontal line as solute concentration in the effluent maximizes.

The equilibrium concentration of solutes in the effluent will remain substantially constant as the feed solution is passes through the matrix, as long as binding sites remain available. Eventually, however, the binding sites of the matrix become saturated, and the target solute will flow directly through the matrix without net interaction. This is referred to as breakthrough. Thus, the emergence of the target solute from the matrix will result in a detected increase in ultra-violet absorption of the effluent. Thus, when solute concentration reaches a plateau, indicating that the feed is simply flowing through the column without net solute interaction with the matrix surface, the solute concentration in the effluent equals the concentration in the feed.

When a non-diffusively bound chromatography matrix is used, or when liquid flow rates are slow relative to diffusion times, the above-discussed phenomena result in a graph with two well-defined steps. That is, when an equilibrium concentration representative of the concentration of non-target solutes in the effluent is reached, a first well-defined plateau will result. This will be followed by a transition period indicated by a vertical line, or a line with a slope approaching the vertical, and a second plateau representative of the concentration of the target and non-target solutes together.

The difference between these equilibrium concentrations may be used to calculate the concentration of target solute in the sample, as the difference between equilibrium concentration is directly proportional to the concentration of target solute in the sample. Furthermore, since the second plateau is indicative of the additive concentration of all solutes in the feed, that value can be obtained by monitoring the sample prior to the time it enters the matrix. Thus, all information necessary to calculate the target solute concentration is available as soon as a plateau in the breakthrough of non-target or contaminating solute is reached. The device is calibrated by passing through the solute detector known concentrations of pure target solute so that concentration units can be correlated directly with, e.g., absorbance units. The product of the difference between the sensed plateaus and the correlation factor equals the concentration of the target solute.

The matrix preferably is a rigid, substantially non-microporous, particulate material having a hydrophilic surface, and preferably is a perfusive chromatography matrix. The matrix also may be defined by the interior surface of a capillary. Where the matrix comprises surface regions comprising immobilized protein A, protein G, and the binding protein is immunoglobulin, one can remove the binding site from the matrix after each run, and reload the matrix with fresh binding sites. Immunoglobulin and other types of protein binding sites also may be non-specifically adsorbed on a hydrophobic polymer matrix surface and removed with mixed organic/ionic striping solutions.

It is necessary to the proper exploitation of this embodiment of the present invention that a chromatographic technique be used that results in a well-defined breakthrough. This can be achieved readily using essentially any matrix geometry, provided the flow rate through the matrix is slow. At slow flow rates, the time required for solutes to diffuse into and out of the pores of the conventional liquid chromatography or other chromatography medium is insufficient to destroy the development of a distinct concentration plateau in the effluent. However, at higher flow rates using conventional media, the concentration plateaus in the effluent typically are not discernible. This essentially means that, for desired high speed operation, non-diffusion bound chromatographic matrices should be used.

Also, the matrix should be as small as possible. The volume of sample that can be present in the matrix, coupled with the flow rate, dictate the time interval between introduction of the sample and breakthrough. Higher flow rates and small volume columns promote high speed analysis. This approach can result in assays being performed in periods of time substantially less than one minute and easily less than 10 seconds. For all practical purposes, these short time frames can be considered "real time" measurements.

The quantitative analysis technique is independent of flow rate, and does not require the target solute and the matrix to reach equilibrium. Thus, the sample may be impelled through the matrix by any convenient method, e.g., manually, e.g., using a syringe or by an electrically driven pump.

Subtractive chromatography according to the chromatography system of the invention can be performed repeatedly without compromising the accuracy of the process. While an unknown subset of binding sites of the matrix may be degraded with repeated sequences of binding, elution, and reequilibration, the method generates information based on concentration differences of the target and non-target solutes. Thus, the availability of fewer binding sites will translate to earlier target solute breakthrough but will not give inaccurate indications of concentration.

The subtractive method using the apparatus of the invention also affords a self-checking capability and a high degree of flexibility. If detected concentration differs between the feed and the final effluent plateau, the system may be operating improperly. Self-checking also can be implemented by washing the matrix after the final effluent plateau has been reached and then eluting the target solute. Integration of the detected pulse in the eluate will give an indication of the amount of bound target solute, which should correlate with the previous datum. In addition, the method is very flexible. Consider, for example, a situation in which a sample having high concentration of target solute is passed through a matrix. This may result in almost immediate saturation of the binding sites of the matrix, and therefore, almost immediate breakthrough. On a graph like that discussed above, the output will appear as a single vertical line followed by a horizontal plateau, giving no information about the concentration of target or non-target solute. To remedy this situation, the sample need only be diluted with buffer solution or the like. By diluting the sample breakthrough is delayed, thereby affording a clear distinction between the equilibrium concentration of the non-target solute in the effluent and the equilibrium concentration of the target and non-target solute together. If the amount of diluent is known, dilution does not adversely affect the precision or accuracy of the results. Assay of very dilute samples can also be conducted routinely. The only potentially negative effect on the system is that the time required to saturate the binding sites increases. This, of course, is a liability only for the self-checking aspect of the process, as the plateau reached after breakthrough of the target solute can be determined directly from the sample.

Another feature of this embodiment of the invention is that the binding sites on the matrix, e.g., monoclonal or polyclonal antibodies or other binding proteins, can be interchanged readily depending upon the identity of the target solute, using known techniques. This feature permits construction of a single matrix and assay device which can be customized for any target solute.

A further advantage of this embodiment of the invention is that it can be utilized on an extremely small scale. Even microliter sized samples can be analyzed. Moreover, rather than filling a traditional chromatography column with high surface area particles to serve as a matrix, one can coat binding protein on the inner surface of a capillary tube. Passing a solution through the capillary tube can achieve the same results as those discussed above.

Subtractive chromatography according to the chromatography system described herein provides a method for monitoring the production of a solute based on subtractive frontal breakthrough analysis. The method may be performed using the apparatus of the invention as follows.

Referring to FIG. 3, a valve 151 directs either a sample from sample input 118, a buffer solution from any one of reservoirs 111a–c for washing and reequilibrating a chromatography matrix, or an eluant from any one of reservoirs 111e–f capable of inducing release of adsorbed species from binding sites in a chromatography matrix. The output of valve 151 ultimately directs a selected solution through a chromatography matrix, e.g., in column 131, of a nature described herein in more detail, which comprises binding sites disposed about a surface and capable of selectively adsorbing an analyte or target solute sought to be determined. Solute concentration can be detected before or after passage through column 131. Detector 136 may be a conventional device of the type commonly used in chromatography equipment comprising, for example, a U.V. light source which provides a beam through a film of the sample and a U.V. detector which permits measurement of absorption by solutes in the sample. Liquid exiting matrix column 131 enters detector 136 which also measures a parameter characteristic of solute concentration, this time in the effluent, and delivers a signal representative of that quantity through line 146. Data from the detectors enters an electronic calculator means, where, for example, the difference between the sensed absorption maxima in the optional detector and detector 136 is calculated, and that difference is used by multiplication with a conversion factor to determine target solute concentration. The concentration value may also be delivered to a display.

If solute concentration is detected only after passage through column 131, detector 136 detects a first plateau representative of the concentration of non-target solutes or contaminants exiting matrix column 131, and at a later time, after breakthrough of the target solutes, detects total solute concentration. Data points representative of these sensed plateaus are delivered to calculator means 30 and processed as set forth above.

If solute concentration is detected prior to the sample passing through column 131, the sample is shunted directly to detector 136 for pre-column binding measurements via valve 151 (state 2), valve 134 (state 1), and valve 133 (state 2), and effluent from matrix column 131 is shunted directly to detector 136 for post-column binding measurements. This permits a single detector to measure the total solute concentration in the sample prior to its introduction into the column 131, and thereafter to measure the level of the plateau achieved in the effluent prior to breakthrough of the target solute. Signals representative of the solute concentrations sensed by the detector are transmitted to calculator means as disclosed above.

Subtractive chromatography according to the invention proceeds as follows. Prior to beginning an analysis, the system has been filled with a buffer (from one of reservoirs 111a–c) used to equilibrate column 131 and to assure no solute residues remain in detector 136. To initiate an assay, the valve 151 is adjusted to permit the sample to be introduced into the system impelled by a pressure gradient created by a pump or syringe. Target solute begins binding to the binding sites immobilized in the matrix; contaminants which do not bind pass through the matrix and emerge in the effluent. The effluent is passed by column 132 directly to detector 136, where the build-up of contaminants in the effluent is measured. Prior to the time target solute saturates the binding sites in column 131 and begins breaking through into the effluent stream, the concentration of non-target solute(s) or contaminant(s) in the effluent stream reaches a plateau, and a signal indicative of the level of the plateau is passed to a calculator.

At this point, all information needed to calculate the concentration of the target solute is available, and the assay is complete. However, as a check, flow through the system can be continued until the target solute breaks through column 131 and, together with the contaminants, produces a higher plateau which should be equal to the concentration sensed in the sample prior to its introduction into the matrix.

At this point, as an additional self check, if desired, valve 112 can be switched to direct buffer from reservoir 111 through the system, thereby washing the detector(s) and column 131 free of non-specifically adsorbed contaminants but leaving target solute non-covalently bonded to the binding sites in the matrix. After this wash step, valve 112 is again switched to introduce eluent from reservoir 111 through the system. The eluant serves to elute the target solute from the column 131. The eluted target solute is detected by the detector as a pulse of solute. Integration of the pulse curve or other determination of the area under the curve gives an indication of the quantity of target solute bound during the assay which, again, can be correlated to the concentration derived previously. FIG. 14 is a flow chart of the above-described procedure.

From the foregoing, it will be appreciated that design and construction of all components of this system are well within the skill of the art. Indeed, many other configurations suitable for the practice of the process of the invention can be devised, and additional features incorporated as desired. For example, the system can be designed to have replaceable matrix modules, individual ones of which comprise binding sites specific for predetermined target solutes. Since accuracy of the assay is independent of flow rate, it matters not how one chooses to promote flow through the system. Thus, for example, a pump may be placed anywhere in the fluid flow line. Alternatively, the sample may be placed in a syringe and simply rammed through the system.

The calculator means or processor can take various forms, and indeed, in the broader aspects of the invention, is not required. A conventional plotter attached to the detector(s) would permit an operator of a production or purification system to determine visually be observing plural consecutive plots whether concentration of the target solute and/or the impurities is changing with time or is constant. However, the calculator may include means for storing signals representative of data points indicative of the sensed solute concentration ratios, and correlation factors, and an arithmetic calculation module which calculates target solute concentration and/or contaminant solute concentration. These data may be displayed digitally after each assay. Alternatively, the data may be used to produce a plot of target solute concentration over time, or other desired indication of the state of the system, as a record of the dynamic behavior of the system under analysis.

A chromatogram is generated by measuring and charting a characteristic of the effluent that varies in proportion to the concentration of detectable solute in the effluent. In a typical application, commonly used in commercial chromatography equipment, ultra-violet radiation is passed through the effluent and the degree of ultra-violet absorption is charted. Absorption of U.V. light in such systems is proportional to solute concentration, provided the solute is absorptive of this wavelength. It should be understood, however, that any characteristic of the effluent which is representative of the concentrations of analyte and impurities therein can be monitored for purposes of the present invention.

Figure 9:
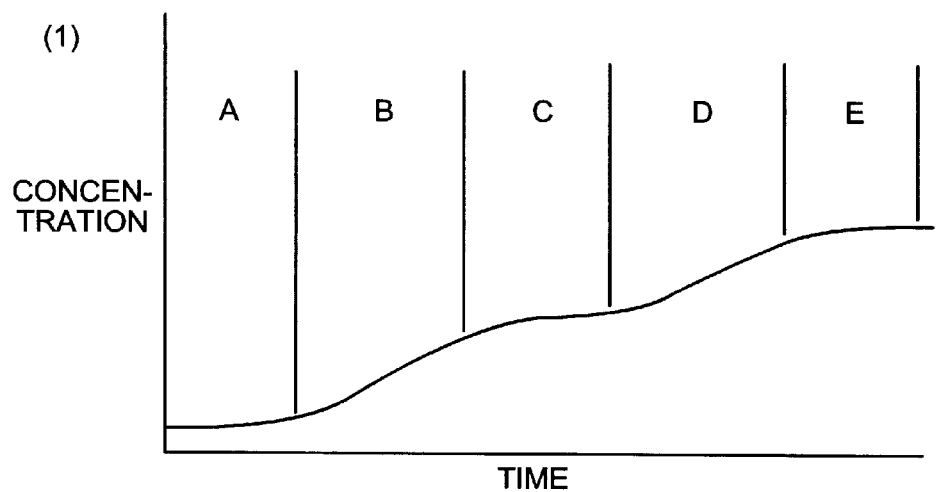
Figure 9:
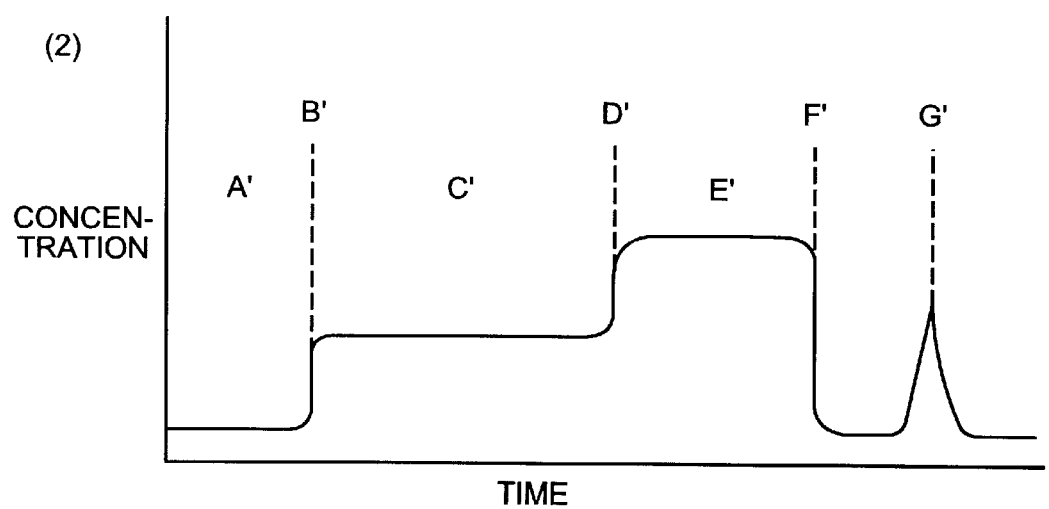

The abcissa of the chromatogram of FIG. 9(1) indicates time, and the ordinate absorption or concentration. For illustrative purposes the graph is divided into five periods which are labelled A, B, C, D, and E. The periods define stages of solute concentration in the effluent during a chromatographic loading cycle that might be encountered when passing a sample through a conventional affinity chromatography matrix housed in a column at a high rate, e.g., 1800 cm/hr. It is easy to see that due to poor resolution the boundaries between periods must be drawn rather arbitrarily.

Initial period A represents the condition where the effluent consists entirely of buffer. When the effluent begins to include impurities from the sample, the solute concentration begins to rise as shown in period B. Eventually, an equilibrium concentration will be reached as depicted in period C. This will occur when non-specific binding (if any) of impurities to the matrix has stopped and target solute is being retained by binding to the matrix so that the concentration of impurities in the feed is equal to the concentration of impurities in the effluent. As sample continues to flow through the matrix, the target solute begins to saturate the binding sites of the matrix. This results in the emergence of target solute in a gradually increasing concentration in the effluent, commonly referred to as "breakthrough", illustrated in period D. When the binding sites are completely saturated (period E), the sample merely flows through the matrix and the concentration of solute in the effluent is equal to the concentration of solute in the feed.

Note that the "plateau" of period C is the critical information necessary to calculate the concentration of the target solute, but that the height of the plateau, and its boundaries, are far from distinct. For samples containing multiple solutes of differing physical properties, the chromatogram can be far less informative, and the faster one passes the sample through the matrix, generally the more the critical plateau is marked by band spreading.

There is shown in FIG. 9(2) a chromatogram typical of that obtained by passing the sample very slowly through the matrix. The single most significant distinction between the graphs of FIGS. 9(1) and (2) is that the latter has sharply defined breakthrough points and equilibrium levels. Period A' of FIG. 9(2) corresponds to period A of FIG. 9(1) and is representative of the period over which buffer alone constitutes the effluent. FIG. 9(2) shows that the matrix becomes saturated with impurities due to non-specific binding over a short interval so that an equilibrium concentration of impurities is reached in period C' at a very well defined point in time. This is represented in the figure as breakthrough point B'. The equilibrium concentration of period C' will be maintained as analyte contained in the solution is loaded onto the binding sites of the matrix until those binding sites become saturated. When this occurs, a second breakthrough point D' will be reached wherein the concentration of the analyte in the effluent will become equal to the concentration of the analyte in the feed solution. The concentration of the analyte and impurities together will be directly proportional to the equilibrium concentration of period E' which follows the second breakthrough step D'. The difference, therefore, between the height of plateau E' and the height of plateau C' can be used to calculate the concentration of analyte in the feed solution.

Additionally, if the capacity of the matrix is known, by monitoring the amount of solution passed through the matrix before the breakthrough step D' occurs, the concentration of analyte in the solution also can be determined. Since, however, over repeated uses the binding capacity (the number of binding sites in the matrix) will decrease, it will more often be the case that the concentration of analyte in the solution will be determined based upon the principles discussed above. The concentration so determined, therefore, can be used in conjunction with the timing of the breakthrough step D' to determine how many binding sites remain in the matrix.

Line F' in FIG. 9(2) represents the point at which solution has ceased being passed through the matrix, and the effluent once again comprises only buffer. A third way to determine the amount of analyte in the solution is during desorption of the analyte from the matrix by way of passing an eluent through the matrix to free the analyte from the binding sites. This process is represented in the figure by the behavior of the chromatogram during period G'. The area under the curve in this period is directly proportional to the amount of analyte bound to the matrix as of the breakthrough point D'.

It is clearly possible, therefore, to check the accuracy of the determination of target solute concentration made based on the height of step D' to that determination made based upon the area under the curve during period G'.

With repeated use the chromatography matrix will breakdown in the sense that its capacity will decrease. This will not, however, affect the accuracy of the data generated in accordance with the principles of the present invention. All that occurs is that the length of plateau C' in FIG. 9(2) becomes shorter, as target solute breaks through sooner. Neither the height of the breakthrough plateau representative of concentration of the impurities nor the solute concentration maxima change, and accuracy is not comprised.

As has been mentioned throughout this description, a preferred aspect of the present invention involves high speed assays, e.g., less than 10 seconds. The above discussed analysis can be performed in periods substantially shorter than one minute, often shorter than 30 seconds, and frequently less than 10 seconds, if one employs a small volume column containing a matrix medium of the type described herein.

EXAMPLE 4

The chromatography system of the invention may be used for detecting differences in the structural profile of a protein in separate samples. The phrase "structural profile", or "fingerprint", as used herein, refers to the particular mix of molecular species in a protein solution, which can vary from batch to batch or over time due to expression errors, truncation by proteases, or differences in post translation modification resulting in variations in conformation or derivatization. Thus, the sample may be passed through a matrix comprising immobilized binding sites which vary with respect to their binding properties and structural variants in the sample. For example, polyclonal antibodies may be used, cloned variants of which are specific for a particular epitope on a particular variant of the protein. Alternatively, a single type of binding site may be used which varies in binding affinity or specificity with variants of the protein to be analyzed. This procedure can produce a breakthrough function characteristic of the structural profile of the protein in the sample as the concentration of protein exiting the matrix is measured after at least some of the binding sites have been saturated with the protein. Comparing the characteristic functions of different samples permits indirect comparison of their structural makeup.

Since molecular subspecies in the protein mix have separate and distinct structural features, each subspecies has at least some unique epitopes. Each fraction of the binding protein in the matrix therefore will be capable of discriminating, (i.e., selectively binding) particular molecular subspecies, or of binding a molecular subspecies preferentially. Thus, as the protein sample is passed through the matrix, various of its subspecies reach equilibrium saturation, and thereafter break through into the effluent. If the protein concentration of effluent is monitored over time, there is an interval over which protein concentration in the effluent increases from a baseline value, typically zero, to a value substantially identical to protein concentration in the feed. During the interval the protein concentration increases progressively in a way that is indicative of the particular structural profile of the protein sample. When this function is compared for separate protein samples, one can determine whether those samples have uniform structure. This method can be used, for example, to monitor a production stream periodically as a means of assuring that the product remains within a predetermined specification.

This procedure is performed substantially as described above in Example 3, except that the effluent from column 131 is passed through a second column 132 after column 131 reaches breakthrough. Column 132 will then separate the breakthrough into molecular subspecies, thus providing a structural profile of the target component of the sample.

The calculator means may be omitted if the purpose of the device is solely to monitor protein structure. In this case, the display is adapted to display a plot of a function representative of protein concentration in the effluent versus a function representative of effluent volume. The display thus produces a curve characteristic of the structural profile of the protein sample which can serve as a "fingerprint" of the sample which will identify a given sample composition and change if the structural profile of the protein changes. FIG. 15 shows a flow chart of steps taken to carry out the procedure described in Example 4.

EXAMPLE 5

The chromatography system of the invention may be used as a rapid monitoring system during preparation of a product, and can quickly provide information as to the presence, concentration, and purity of a sample. This system is based on what is described herein, and in the continuation-in-part application of U.S. Ser. No. 07/566,121, filed Dec. 6, 1991, which is assigned to the same assignee and hereby incorporated by reference. The apparatus of the invention useful for this type of rapid monitoring procedure is shown in FIGS. 4(a) and (b) and includes at least two multiport valves, one column, and one detector.

A defined sample volume, e.g., from a process stream which may having continuously changing concentrations of solutes, is fed through input 14 to valve 151, where it is then fed through sample loop 152 and line 42 to valve 133, and then to sample loop 153. A portion of the sample is collected and held in loop 153 by switching of valves 151 and 133. The sample contained within loop 152 has been diverted (by switching valve 151 to State 2) through column 131 for adsorption of target solute. As the defined volume of the feed solution passes through the matrix, the target solute will adsorb at the binding sites, thereby virtually eliminating any concentration of the target solute in the effluent. Once target solute has been adsorbed from the sample contained in loop 152, the adsorbed sample exits the column and is fed in-line behind non-adsorbed sample remaining in loop 153, which is also in state 2. Both non-adsorbed and then adsorbed sample are then fed into detector 136.

Display of the chromatographic results will reveal a first peak representing a high concentration of the original non-adsorbed sample followed by a second smaller peak having a decrease in peak height and area proportional to the amount of target solute removed by column 131 and representing the impurities remaining in the sample after adsorption. If desired, the target solute may then be eluted and detected, as described above.

Since only a small amount of sample is required in this embodiment of the invention, i.e., enough sample to fill sample loops 152 and 153, the amount of target solute contained in the sample preferably never saturates the binding sites in column 131, as long as the capacity of the column is much larger than the amount of target solute in the sample volume.

Figure 10A:
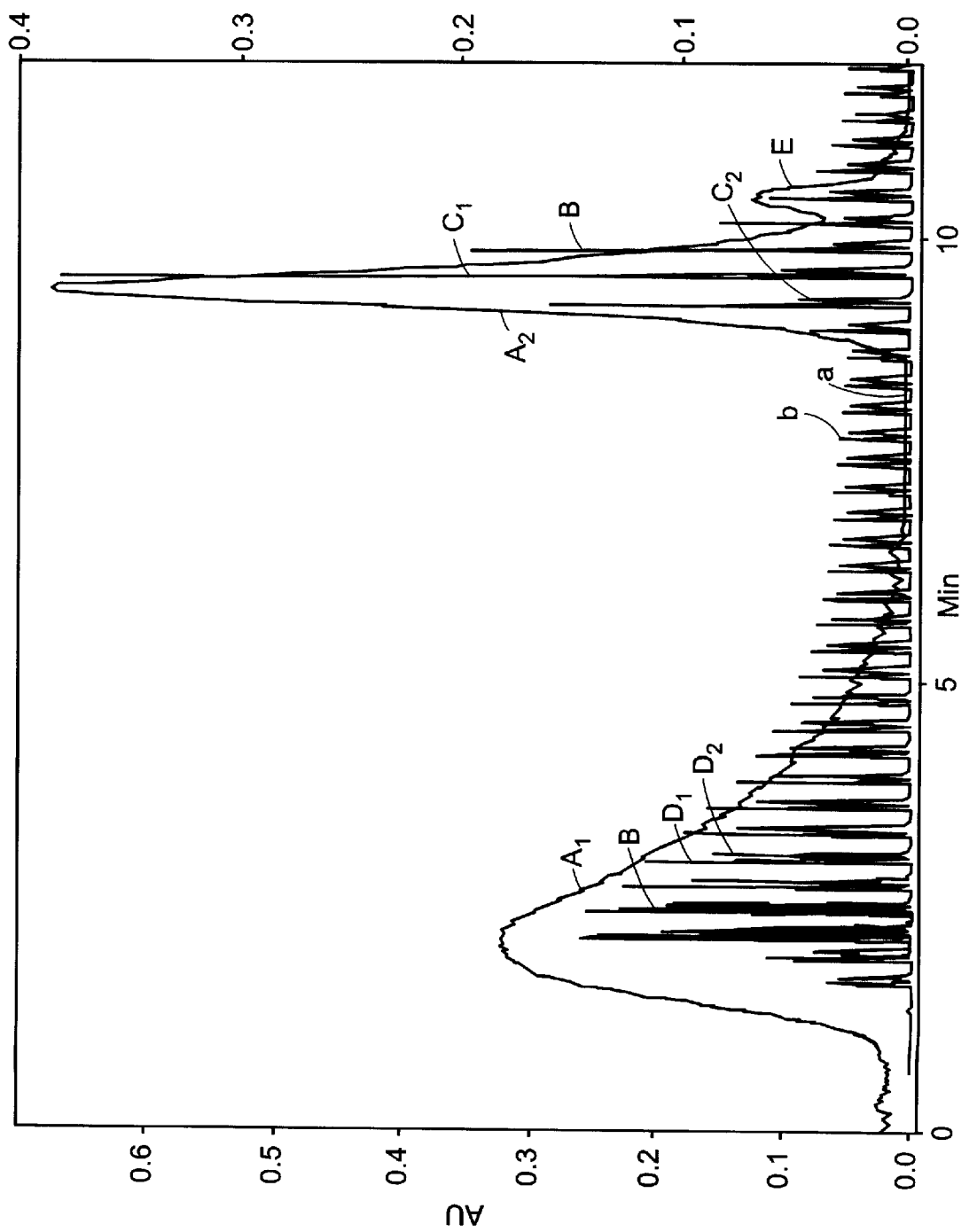

To demonstrate practice of the invention in quickly determining the concentration of a target solute in a sample, a continuous stream of effluent from a preparative chromatography column was sampled at regular intervals of 15 seconds, using the apparatus shown in FIG. 4. IgG from cell culture supernatant was purified using a POROS HS/M 10×100 mm column (PerSeptive Biosystems, Inc., Cambridge, Mass.) and the Delta Prep HPLC System (Waters, Milford, Mass.). Preparative chromatography was performed using MES buffer, pH 6.2 with and without 1N NaCl. In FIGS. 10(a) and (b), preparative chromatogram tracing "A1" and "A2" is shown and has two major peaks, a broad peak ("A1") 0–5 min. of FIG. 10(a) and run numbers 2–16 in FIG. 10(b), and a sharp peak ("A2") between 8–10 min. in FIG. 10(a) and run numbers 29–34 in FIG. 10(b). The preparative tracing ("A1" and "A2") was generated rising an absorbance detector set a 280 nm. The location of IgG in this chromatogram is difficult to determine, as is the purity of the sample.

During preparative chromatography, the process stream flowing from the preparative column was sampled by taking defined aliquots at regular 15 sec. intervals, and each sample analyzed for its purity of IgG. FIG. 10(a) shows an overlay of analytical traces (i.e., the doublet spike peaks designated "B") which were obtained using the rapid monitoring apparatus shown in FIG. 4, and which provide all the information that is needed to determine the amount of IgG and impurities in each sample aliquot. 20 µl sample aliquots were pumped through the column at 2 ml/min. Sample loops 152, 153 were capable of holding 20 µl in this procedure. The affinity column 131 was a 2.1×30 mm Protein G column which has approximately 1.5 mg of binding capacity for human IgG. The detector 136 was set at 220 nm for high sensitivity. The sample was chased through the system using phosphate buffered saline (PBS) at pH 7.0.

In the chromatogram of FIG. 10(a), each spike doublet corresponds to a single sample aliquot, the spike to the left within the doublet corresponding to absorbance of the sample as it comes off of the preparative column and the spike to the right within the doublet corresponding to absorbance of the sample after it has passed through the column. There is a background level of absorbance at 220 nm due to the buffers used both in the preparative column (MES buffer), and the rapid analysis chase buffer (a phosphate buffer). This background absorbance is evident in the doublet peaks at time 8.1 minutes and 8.4 minutes ("b"), where this portion of the preparative chromatographic tracing ("a") shows the absence of protein, yet there continues to be an absorbance signal ("b"). In the area of the chromatogram where protein is present (i.e., the large peaks designated "B"), the purity of IgG in each sample aliquot can be determined by taking the difference in height of the peak (or area under the peak) between the first and second peaks of each doublet. For example, the doublet occurring at about 9.5 min. is clearly in an area of the chromatogram where protein is present, and includes two peaks of very different height ("C1" and "C2"). The difference in the area of peak "C1" and "C2" indicates the amount of IgG in that sample aliquot, whereas the area under peak "C2" is proportional to the amount of impurities in that sample aliquot. This is also true of the doublets which occur between 9.0 and 10.5 minutes. This large difference in height between the peaks of each doublet indicates that IgG is present in these sample aliquots. In contrast, each doublet occurring between 1.5 and 3 minutes, which also clearly contain protein, contain peaks which are closer in height (e.g., "D1" and "D2"), indicating that relatively little IgG is present in the sample. There is an estimated delay time between the preparative signal ("A") and the analytical doublets ("B") of about 0.13 minutes or 0.65 ml.

The total duration of the main eluted peak ("A2") is about 2 minutes, 10 mls, or 1 column volume. The minor eluted peak ("E"), which is most likely bovine serum albumin, is 0.5 minutes in duration. The analysis at time 10.5 minutes is reflective of the purity at the first half of this peak while the one at time 10.75 minutes assays the last half. Clearly, some IgG is found contaminating the first half of this peak. This is consistent with the profile of the preparative chromatogram in which the IgG peak elutes with a significant tail.

Figure 10B:
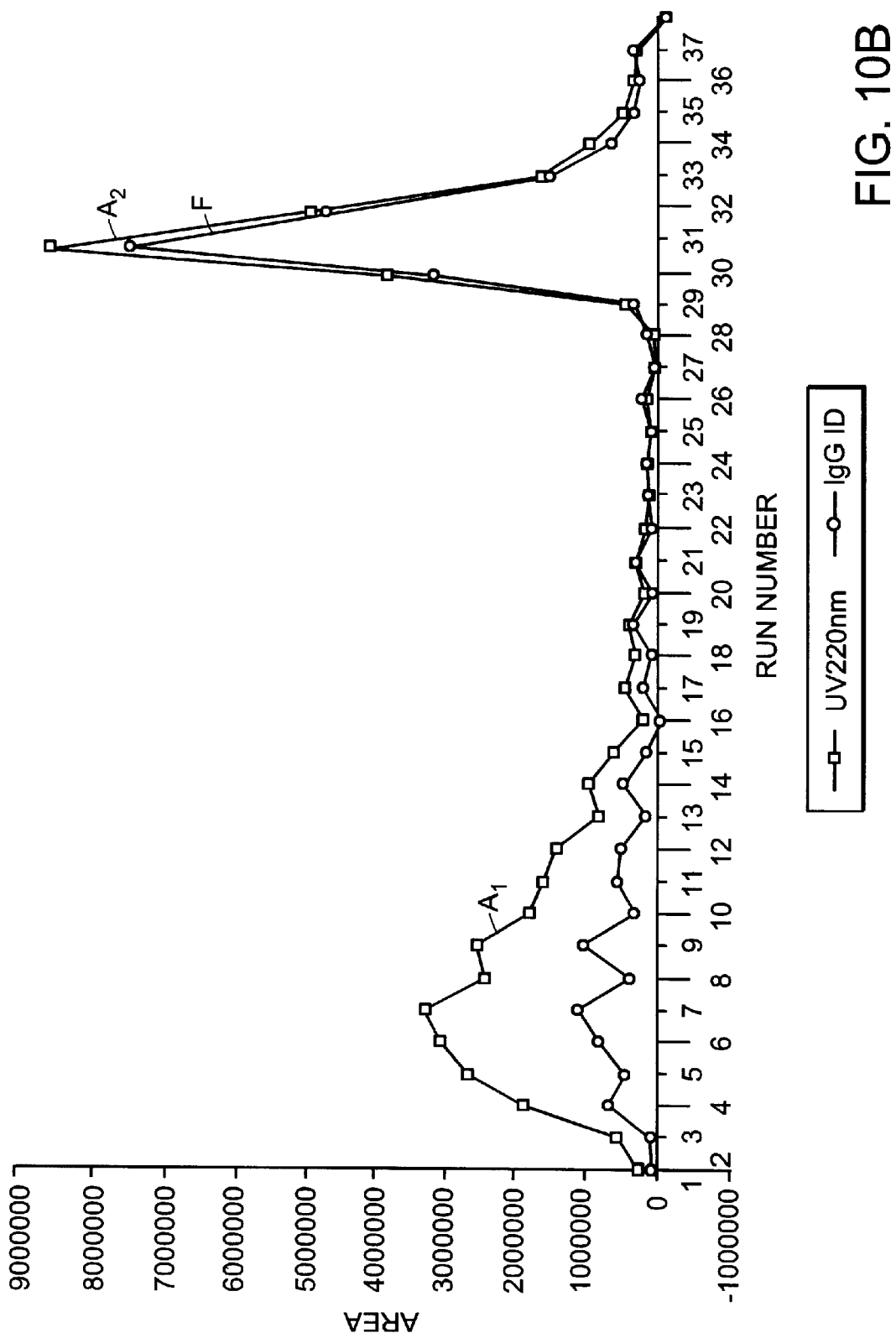

FIG. 10(b) shows both the preparative tracing ("A1" and "A2") shown in FIG. 10(a), as well as the area under each peak corresponding to the amount of target solute (IgG) removed from the sample in the column of FIG. 4. The latter was obtained by subtracting the smaller spike of each doublet from the taller spike in FIG. 10(a), e.g., peak "C2" from "C1". The samples of FIG. 10(b) have also been normalized to zero level background by subtracting the MES and phosphate buffer absorbance from the peak area. In FIG. 10(b), the IgG peak ("F") is clearly co-eluting with the main preparative peak ("A2") and its purity is greater than 80% during analytical runs 28, 29 and 30. Analytical runs 31 and 32 report greater than 95% purity. Therefore, while a contaminant co-elutes with the first part of the IgG peak, the second half is essentially pure.

The rapid monitoring method can provide on-line analytical information about the presence, quantity and purity of a product. In addition to monitoring, this system can both accept input commands and send out control commands. Specifically, when used to monitor a production scale chromatography column typically with a 3–4 hour runtime, the process UV monitor can be used to trigger the start of the analysis. That is, an increase in UV signal above baseline triggers analysis. Furthermore, when rapid process monitoring detects a product above a given purity, it can send a contact closure signal starting fraction collection of the preparative run. Finally, when the product concentration or purity falls below a defined level, the fraction collector can be signalled to discontinue. This capability is valuable in operations when a column is used in a rapid cycling mode. Furthermore, the reduction is analytical burden and in downtime to determine the next step can be extremely beneficial in bioprocessing.

In addition to monitoring preparative chromatography, rapid process monitoring can be used to determine product levels in other bioprocessing steps, for example, subtractive detection to monitor contaminants including other proteins, DNA or endotoxins. In each case, protein binding pairs exist so a column-based target protein subtraction can be easily performed.

EXAMPLE 6

The chromatography system and apparatus of the invention may be used to monitor any preparative procedure during the preparative process. For example, if a preparative run is occurring in column 131, the preparative process can be interrupted at any time during the run to analyze the effluent at the selected time. Such analysis will aid in making decisions on how the preparation is proceeding. Information will thus become available as to, e.g., if the sample needs to be diverted back to column 131, if the process is complete and the solute of interest is pure, or if the process is not working properly.

Figure 11A:
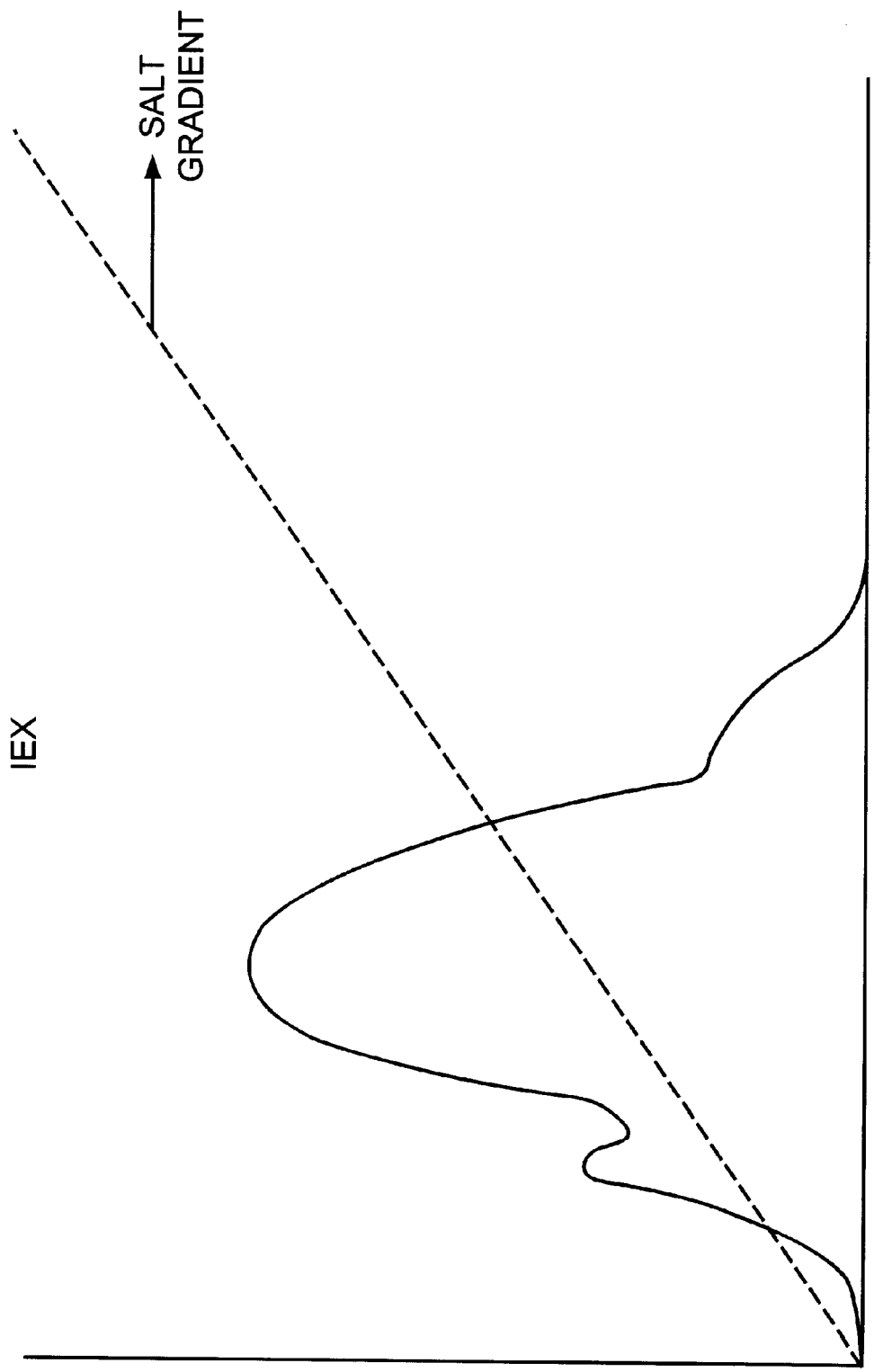
Figure 11B:
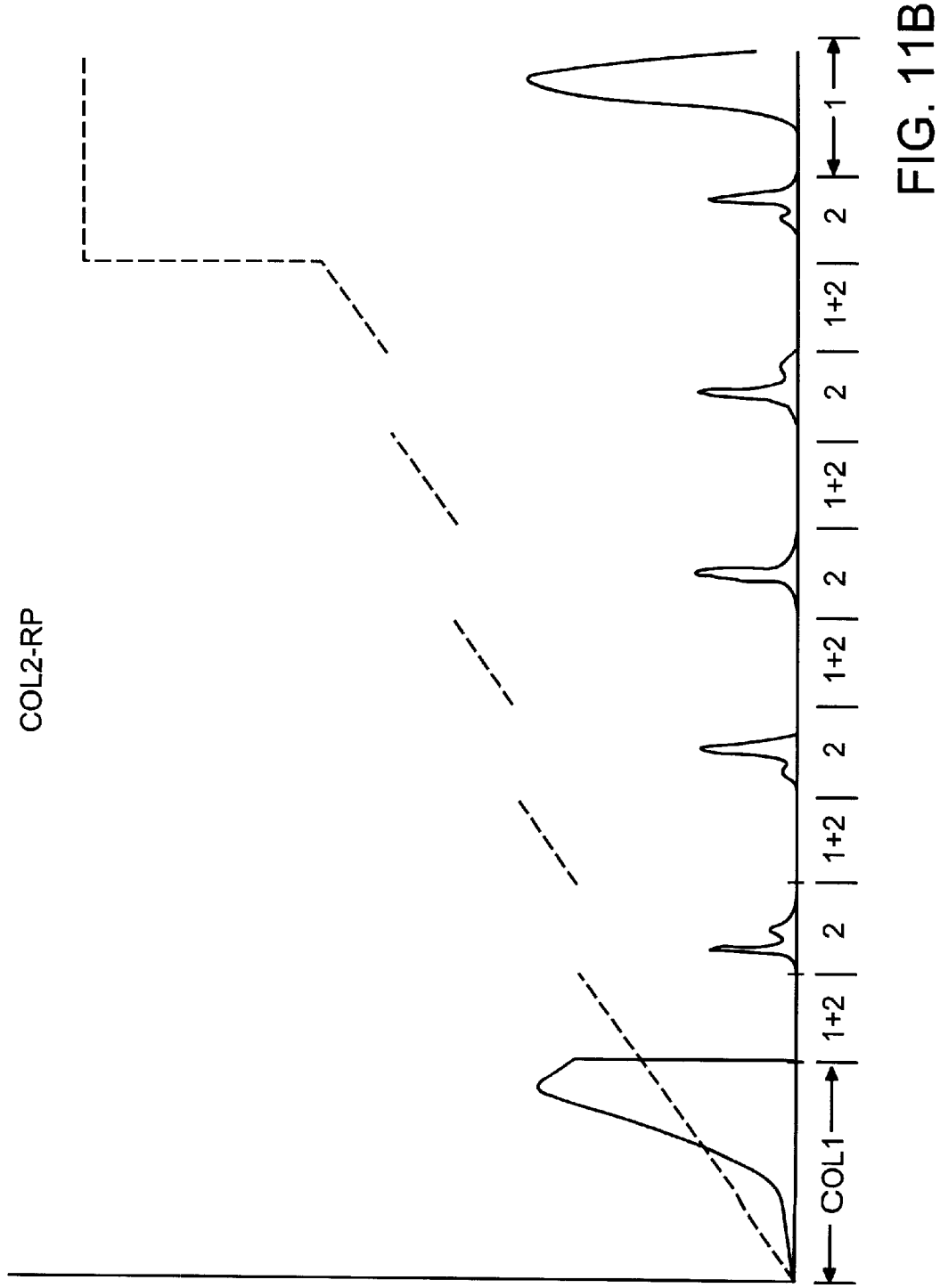

The apparatus may be utilized for a preparative/analytical process as follows. After the columns have been equilibrated, the sample will pass through valves 151 and 134 into column 131, e.g., an ion exchange column. The effluent from column 131 may be monitored by bypassing column 132 via valve 133 as described in the examples above. A read-out of effluent from column 131 may be obtained in detector 136. At any chosen moment in the procedure, a fraction of the effluent from column 131 may be analyzed by switching valve 133 to the position in which it feeds into column 132. The effluent fraction will then be passed over column 132, e.g, a reverse phase chromatography column. The flow to the ion exchange column 131 is stopped, and the column 132 (reverse phase) is eluted and analyzed via detector 136. After the analysis is complete on column 132, the flow through column 131 is resumed; e.g., in a manner of seconds, valve 133 is switched back to the position in which it bypasses column 132 and feeds directly to detector 136. FIG. 11(a) shows a chromatogram in which the effluent from column 131 is shown, and FIG. 11(b) shows a chromatogram in which the analytical fraction from column 132 is shown. The major peak in FIG. 11(a) is the product peak and the two smaller peaks on either side of the major peak are contaminant peaks. If the eluant from column 131 is taken at different time points during purification of the major peak, each eluant fraction will contain differing compositions of purity of the major peak with respect to the minor peaks. These fractions are analyzed on column 132 and are shown as different time points in FIG. 11(b). Below each time point is shown the configuration of the columns, e.g., if column 1 (131) or 2 (132) or both are on-line. FIG. 15 is a flow chart of steps which may be taken to perform this procedure.

It will be understood that the above descriptions are made by way of illustration, and that the invention may take other forms within the spirit of the structures and methods described herein. Variations and modifications will occur to those skilled in the art, and all such variations and modifications are considered to be part of the invention, as defined in the claims.

What is claimed is:

1. An apparatus for the separation of proteins in a sample, said apparatus comprising sample solution input means, a first liquid chromatography column, at least one multiport injection valve connecting said sample solution input means to said column, a second liquid chromatography column in communication with said multiport injection valve, said second column being operative successively with or alternatively to said first column, at least one of said first and second columns being packed with a particulate chromatography material comprising perfusive particles which permit convective fluid transport both within and between the particles, or non-porous particles, thereby to confer on said column a chromatographically effective mobile phase transit time therethrough less than five minutes, pump means for providing variable pressure delivery of solutions to said columns via said multiport valve, plural solution reservoirs, a mixing valve, connecting said solution reservoirs to said columns, operative to mix solutions from said reservoirs, and program means for specifying a sequence of system control programs, the mixing of solution by said mixing valve, and the delivery of said mixed solution to said columns via said multiport injection valve.

2. The apparatus of claim 1, further comprising control means in communication with said pump means for controlling the pressure of delivery of said solution.

3. The apparatus of claim 1, further comprising
   detector means for detecting and recording column output.

4. The apparatus of claim 3, further comprising template matching means for identifying a pattern of detected output data, said template matching means being operatively keyed to means for developing a control program for chromatographic separation.

5. An apparatus for the separation of proteins in a sample, comprising a multiport mixing valve for mixing sample with one or more buffers to produce a sample mix, plural liquid chromatography columns packed with a particulate chromatography material comprising perfusive particles which permit convective fluid transport both within and between the particles, or non-porous particles, thereby to confer on said columns a chromatographically effective liquid phase transit time therethrough less than five minutes, each said column comprising a first and a second end, a multiport injection valve in communication with said sample mixing valve and said first end of each of said liquid chromatography columns, an output system comprising an output signal recording system and an output sample collection system, wherein said output system is in communication with said second end of each of said columns, and control means for operating said multiport injection valve to successively and alternately apply a mixed solution from the mixing valve to one of said respective columns in coordination with operation of said output system to run a sequence of separations for the preparation or analysis of a protein.

6. The apparatus of claim 5, further comprising
   a sample input system comprising plural solution reservoirs and a sample reservoir.

7. The apparatus of claim 5 wherein said control means further comprises
   switching means for alternatively utilizing one of said plural liquid chromatography columns while cleaning another, thus providing a substantially continuous operating sequence of outputs from successively utilized columns.

8. The apparatus of claim 5 further comprising
   program means for specifying a sequence of separation process control programs to be successively run during operation.

9. The apparatus of claim 8 wherein said program means specifies a separation program in which first and second columns are utilized successively for separating proteins in said sample.

10. The apparatus of claim 9 wherein one said column comprises an ion exchange chromatography matrix.

11. The apparatus of claim 9 wherein one said column comprises a reverse phase chromatography matrix.

12. The apparatus of claim 8 wherein said program specifies substantially continuous preparation of a separated sample in said first column and intermittent analysis of said first column output via said second column.

13. The apparatus of claim 5 wherein at least one of said plural columns is removable and replaceable by a different column.

14. An apparatus for the quantitative detection of proteins in a sample, comprising first and second multiport valves, each said valve comprising a sample loop which holds a defined volume of sample and connects two ports of said valve;

a liquid chromatography column in communication with said valve, said column being packed with a particulate chromatography material comprising perfusive particles which permit convective fluid transport both within and between the particles, or nonporous particles, thereby to confer on said column a chromatographically effective mobile phase transit time therethrough less than five minutes;

a sample feed line in communication with each said valve;

detector means in communication with said column for detecting output; and control means for operating said multiport valves to switch between
- a collection line comprising said sample feed line, wherein plural sample volumes are introduced into said sample loops and
- a detection line comprising said chromatography column, wherein one sample volume is passed directly through said detector means and another is passed through said column and said detector means.

15. The apparatus of claim 14, wherein said collection line comprises in successive order
   (a) a first sample loop connecting within said first valve a first port and a second port,
   (b) said sample feed line, said feed line connecting an exit port in said first valve with an entry port of said second valve, and
   (c) a second sample loop connecting within said second valve an entry port and an exit port.

16. The apparatus of claim 14 wherein said detection line comprises in successive order
   (a) a first sample loop connecting within said first valve a first port and a third port,
   (b) said chromatography column, said column connecting said third port of said first valve with a third port of said second valve, and
   (c) a second sample loop connecting within said second valve said third port to said detector means.

17. The apparatus of claim 14 wherein said apparatus further comprises a third multiport valve and said chromatography column is in communication with said first and second valves through said third valve.

* * * * *